(12) United States Patent
Bazargan et al.

(10) Patent No.: US 11,735,305 B2
(45) Date of Patent: Aug. 22, 2023

(54) AUTOMATIC CONFIGURATION OF USER-SPECIFIC DATA BASED ON PLACEMENT INTO SERVICE

(71) Applicant: Medtronic MiniMed, Inc., Northridge, CA (US)

(72) Inventors: Afshin Bazargan, Simi Valley, CA (US); Patrick E. Weydt, Moorpark, CA (US); Hans K. Wenstad, Santa Clarita, CA (US); Adam S. Trock, Simi Valley, CA (US); Seung C. Shin, Los Angeles, CA (US); Samuel Finney, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 17/212,956

(22) Filed: Mar. 25, 2021

(65) Prior Publication Data
US 2021/0407644 A1 Dec. 30, 2021

Related U.S. Application Data

(60) Provisional application No. 63/044,993, filed on Jun. 26, 2020.

(51) Int. Cl.
*G08B 21/04* (2006.01)
*G16H 20/17* (2018.01)
(Continued)

(52) U.S. Cl.
CPC .......... *G16H 20/17* (2018.01); *A61M 5/1723* (2013.01); *G16H 40/67* (2018.01);
(Continued)

(58) Field of Classification Search
USPC .... 340/539.12, 539.14, 539.22, 588, 636.11, 340/665, 691.7, 825.19, 5.52, 5.82, 7.5,
(Continued)

(56) References Cited

U.S. PATENT DOCUMENTS

| 4,562,751 A | 1/1986 | Nason et al. |
| 4,685,903 A | 8/1987 | Cable et al. |

(Continued)

FOREIGN PATENT DOCUMENTS

| CA | 2933166 C | 10/2020 |
| CN | 107615396 B | 6/2022 |
| WO | 2014/035570 A2 | 3/2014 |

OTHER PUBLICATIONS

"Glucose meter," Wikipedia the free encyclopedia, last edit made on May 31, 2020, retrieved from https://en.wikipedia.org/w/index.php?title=Giucose_meter&oldid=959883605, accessed on Sep. 13, 2021, 12 pp.

(Continued)

*Primary Examiner* — Daniel Previl
(74) *Attorney, Agent, or Firm* — Weaver Austin Villeneuve & Sampson LLP

(57) ABSTRACT

A method for automatically configuring a medical device with user-specific configuration data includes determining, by a first medical device, that the first medical device is being placed into service to provide medical therapy to a patient, wherein the first medical device is a replacement medical device for a second medical device that was previously placed into service to provide medical therapy to the patient in accordance with user-specific configuration data stored on the second medical device, communicating, by the first medical device, data indicative of the first medical device being placed into service, after communicating the data indicative of the first medical device being placed into service, obtaining, by the first medical device, the user-
(Continued)

specific configuration data stored on the second medical device, and configuring, by the first medical device, the first medical device to provide therapy in accordance with the obtained user-specific configuration data.

20 Claims, 11 Drawing Sheets

(51) Int. Cl.
  *G16H 40/67* (2018.01)
  *A61M 5/172* (2006.01)
  *A61M 5/142* (2006.01)
(52) U.S. Cl.
  CPC ............ *A61M 2005/14252* (2013.01); *A61M 2205/3327* (2013.01); *A61M 2205/3553* (2013.01); *A61M 2205/52* (2013.01); *A61M 2230/201* (2013.01)
(58) Field of Classification Search
  USPC ..................................................... 340/286.07
  See application file for complete search history.

(56) References Cited

U.S. PATENT DOCUMENTS

| | | | |
|---|---|---|---|
| 5,080,653 A | 1/1992 | Voss et al. | |
| 5,097,122 A | 3/1992 | Colman et al. | |
| 5,505,709 A | 4/1996 | Funderburk et al. | |
| 6,088,608 A | 7/2000 | Schulman et al. | |
| 6,119,028 A | 9/2000 | Schulman et al. | |
| 6,485,465 B2 | 11/2002 | Moberg et al. | |
| 6,488,643 B1 * | 12/2002 | Tumey ................. | A61F 5/0111 601/150 |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,589,229 B1 * | 7/2003 | Connelly .......... | A61M 5/14248 604/890.1 |
| 6,641,533 B2 | 11/2003 | Causey, III et al. | |
| 6,659,980 B2 | 12/2003 | Moberg et al. | |
| 6,740,072 B2 | 5/2004 | Starkweather et al. | |
| 6,752,787 B1 | 6/2004 | Causey, III et al. | |
| 6,817,990 B2 | 11/2004 | Yap et al. | |
| 6,827,702 B2 | 12/2004 | Lebel et al. | |
| 6,932,584 B2 | 8/2005 | Gray et al. | |
| 7,323,142 B2 | 1/2008 | Pendo et al. | |
| 7,402,153 B2 | 7/2008 | Steil et al. | |
| 7,621,893 B2 | 11/2009 | Moberg et al. | |
| 8,674,288 B2 | 3/2014 | Hanson et al. | |
| 9,526,834 B2 * | 12/2016 | Keenan .............. | A61B 5/14503 |
| 10,159,786 B2 | 12/2018 | Smith | |
| 10,238,794 B2 | 3/2019 | Kamen et al. | |
| 2002/0126036 A1 * | 9/2002 | Flaherty ............ | A61B 5/14532 340/870.07 |
| 2011/0218495 A1 * | 9/2011 | Remde .................. | G16H 20/17 604/151 |
| 2011/0231204 A1 | 9/2011 | De La Huerga | |
| 2014/0066889 A1 | 3/2014 | Grosman et al. | |
| 2015/0317855 A1 | 11/2015 | Sezan et al. | |
| 2016/0321400 A1 | 11/2016 | Durrant et al. | |
| 2018/0317826 A1 | 11/2018 | Muhsin et al. | |

OTHER PUBLICATIONS

"Insulin pump," Wikipedia the free encyclopedia, last edit made on Jun. 13, 2020, retrieved from https://en.wikipedia.org/w/index.php?title=Insulin_pump&oldid=962359925, accessed on Sep. 13, 2021, 11 pp.
International Search Report and Written Opinion of International Application No. PCT/US2021/037332, dated Oct. 5, 2021, 17 pp.
U.S. Appl. No. 17/345,538, filed Jun. 11, 2021, naming inventors Bazargan et al.
U.S. Appl. No. 17/212,982, filed Mar. 25, 2021, naming inventors Bazargan et al.
U.S. Appl. No. 17/213,003, filed Mar. 25, 2021, naming inventors Bazargan et al.

\* cited by examiner

US 11,735,305 B2

AUTOMATIC CONFIGURATION OF USER-SPECIFIC DATA BASED ON PLACEMENT INTO SERVICE

This application claims the benefit of U.S. Provisional Application No. 63/044,993, filed Jun. 26, 2020, the entire content of which is hereby incorporated by reference.

TECHNICAL FIELD

The disclosure relates to device autoconfiguration and, more particularly, to automatic configuration of user-specific data.

BACKGROUND

While they are in service, many devices update the information they store about their users. For example, in the medical device field, therapies are often tailored to the idiosyncrasies of patients. Thus, when devices are rotated out of service, replacement devices may not be configured with updated information.

To address this problem, the replacement devices can be manually configured with the updated information. However, the tedious task of manually configuring replacement devices may result in user frustration and improper configuration.

SUMMARY

Devices, systems, and techniques for device autoconfiguration are described. This disclosure describes example techniques to automate transfer of user-specific configuration data from a first device (e.g., an "in-use" insulin pump) to a second device (e.g., a replacement insulin pump). This enables a substantially seamless handoff between the devices.

In one example, the disclosure describes a method for automatically configuring a medical device with user-specific configuration data, the method comprising determining, by a first medical device, that the first medical device is being placed into service to provide medical therapy to a patient, wherein the first medical device is a replacement medical device for a second medical device that was previously placed into service to provide medical therapy to the patient in accordance with user-specific configuration data stored on the second medical device, communicating, by the first medical device, data indicative of the first medical device being placed into service, after communicating the data indicative of the first medical device being placed into service, obtaining, by the first medical device, the user-specific configuration data stored on the second medical device, and configuring, by the first medical device, the first medical device to provide therapy in accordance with the obtained user-specific configuration data.

In one example, the disclosure describes a system for automatically configuring a medical device with user-specific configuration data, the system comprising one or more processors, and one or more processor-readable storage media storing instructions which, when executed by the one or more processors, cause performance of determining that a first medical device is being placed into service to provide medical therapy to a patient, wherein the first medical device is a replacement medical device for a second medical device that was previously placed into service to provide medical therapy to the patient in accordance with user-specific configuration data stored on the second medical device, communicating data indicative of the first medical device being placed into service, after communicating the data indicative of the first medical device being placed into service, obtaining the user-specific configuration data stored on the second medical device, and configuring the first medical device to provide therapy in accordance with the obtained user-specific configuration data.

In one example, the disclosure describes one or more non-transitory processor-readable storage media storing instructions which, when executed by one or more processors, cause performance of determining that a first medical device is being placed into service to provide medical therapy to a patient, wherein the first medical device is a replacement medical device for a second medical device that was previously placed into service to provide medical therapy to the patient in accordance with user-specific configuration data stored on the second medical device, communicating data indicative of the first medical device being placed into service, after communicating the data indicative of the first medical device being placed into service, obtaining the user-specific configuration data stored on the second medical device, and configuring the first medical device to provide therapy in accordance with the obtained user-specific configuration data.

In one example, the disclosure describes a method for automatically configuring a medical device with user-specific configuration data, the method comprising determining, by a first medical device, that the first medical device is being removed from service, wherein the first medical device was previously placed into service to provide therapy to a patient in accordance with user-specific configuration data stored on the first medical device, and wherein the first medical device is to be replaced with a second medical device that is a replacement medical device for the first medical device, and causing, by the first medical device in response to determining that the first medical device is being removed from service, configuration of the second medical device to provide therapy to the patient in accordance with the user-specific configuration data, wherein causing configuration of the second medical device comprises communicating the user-specific configuration data toward the second medical device.

In one example, the disclosure describes a system for automatically configuring a medical device with user-specific configuration data, the system comprising one or more processors, and one or more processor-readable storage media storing instructions which, when executed by the one or more processors, cause performance of determining that a first medical device is being removed from service, wherein the first medical device was previously placed into service to provide therapy to a patient in accordance with user-specific configuration data stored on the first medical device, and wherein the first medical device is to be replaced with a second medical device that is a replacement medical device for the first medical device, and in response to determining that the first medical device is being removed from service, causing configuration of the second medical device to provide therapy to the patient in accordance with the user-specific configuration data, wherein causing configuration of the second medical device comprises communicating the user-specific configuration data toward the second medical device.

In one example, the disclosure describes one or more non-transitory processor-readable storage media storing instructions which, when executed by one or more processors, cause performance of determining that a first medical device is being removed from service, wherein the first medical device was previously placed into service to provide therapy to a patient in accordance with user-specific configuration data stored on the first medical device, and wherein the first medical device is to be replaced with a second medical device that is a replacement medical device for the first medical device, and in response to determining that the first medical device is being removed from service, causing configuration of the second medical device to provide therapy to the patient in accordance with the user-specific configuration data, wherein causing configuration of the second medical device comprises communicating the user-specific configuration data toward the second medical device.

In one example, the disclosure describes a method for automatically configuring a medical device with user-specific configuration data, the method comprising obtaining, by a charger device from one or more server computing devices, user-specific configuration data stored on a first medical device that is configured to provide therapy to a patient in accordance with the user-specific configuration data, and causing, by the charger device, configuration of a second medical device based on communicating the user-specific configuration data to the second medical device while the second medical device is being charged by the charger device, wherein the second medical device is a replacement device for the first medical device.

In one example, the disclosure describes a system for automatically configuring a medical device with user-specific configuration data, the system comprising one or more processors, and one or more processor-readable storage media storing instructions which, when executed by the one or more processors, cause performance of obtaining, from one or more server computing devices, user-specific configuration data stored on a first medical device that is configured to provide therapy to a patient in accordance with the user-specific configuration data, and causing configuration of a second medical device based on communicating the user-specific configuration data to the second medical device while the second medical device is being charged by the charger device, wherein the second medical device is a replacement device for the first medical device.

In one example, the disclosure describes one or more non-transitory processor-readable storage media storing instructions which, when executed by one or more processors, cause performance of obtaining, from one or more server computing devices, user-specific configuration data stored on a first medical device that is configured to provide therapy to a patient in accordance with the user-specific configuration data, and causing configuration of a second medical device based on communicating the user-specific configuration data to the second medical device while the second medical device is being charged by the charger device, wherein the second medical device is a replacement device for the first medical device.

The details of one or more aspects of the disclosure are set forth in the accompanying drawings and the description below. Other features, objects, and advantages of this disclosure will be apparent from the description and drawings, and from the claims.

DETAILED DESCRIPTION

Figure 1:
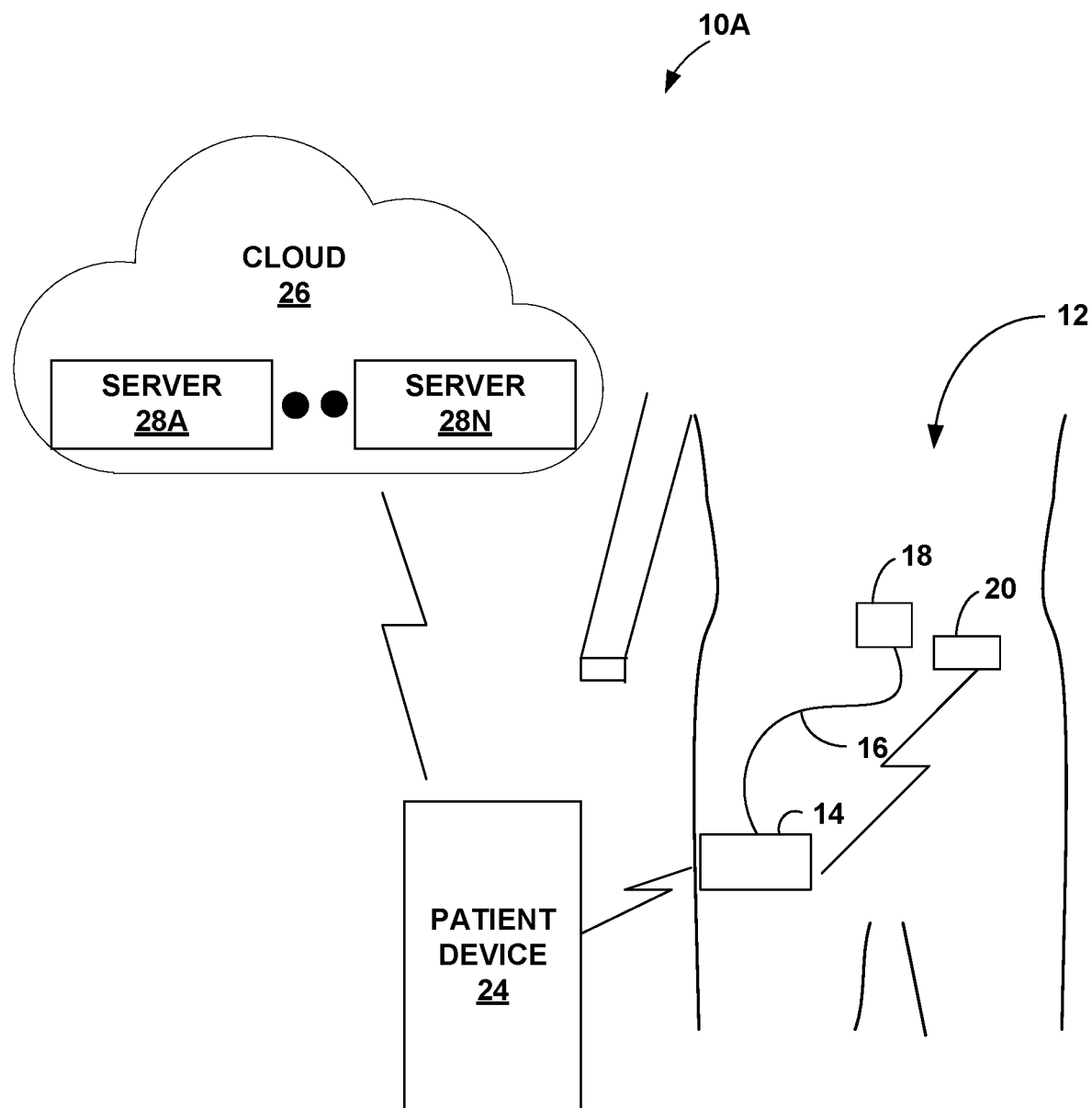
FIG. 1 is a block diagram illustrating an example glucose level management system comprising a tethered pump, in accordance with one or more examples described in this disclosure.

Devices, systems, and techniques for device autoconfiguration are described in this disclosure. Although the subject matter of this disclosure is explained using medical devices as examples, it should be appreciated that the subject matter of this disclosure is not limited to medical devices and is equally applicable to any other devices, including wearable devices and other consumer electronic devices. Furthermore, it should be appreciated that the techniques disclosed herein can be practiced with one or more types of insulin (e.g., fast-acting insulin, intermediate-acting insulin, and/or slow-acting insulin). Thus, terms such as "basal insulin" and "bolus insulin" do not necessarily denote different types of insulin. For example, fast-acting insulin may be used for both basal dosages and bolus dosages.

In some examples, a user (e.g., a patient) may employ medical devices (e.g., patch pumps and/or glucose monitoring devices) for glucose level management, and the medical devices may be configured with user-specific configuration data (e.g., configuration data that may be different for different users). Examples of user-specific configuration data include, without limitation, information indicative of any of the following: insulin-on-board, insulin type, a safe basal rate, one or more insulin delivery rate limits, one or more glucose sensor calibration factors, and an insulin sensitivity factor. User-specific configuration data may be stored in volatile memory and/or non-volatile memory.

Additionally, user-specific configuration data may be updated while the medical device is in use.

In some examples, the user may possess multiple medical devices of the same type (e.g., having the same manufacturer and model number but different serial numbers). Thus, the user may periodically replace (e.g., swap, cycle, or rotate out) an "in-use" medical device with a replacement medical device of the same type when the in-use medical device approaches an inoperable state (e.g., due to a low battery level, an occluded cannula, and/or an empty insulin reservoir). The term "in-use" should not be considered as limited to a device that is currently in use. For example, in some contexts, the term "in-use" may refer to the most recently used device.

When the user switches from the in-use medical device to the replacement medical device, the replacement medical device may not have the most up-to-date user-specific configuration data. Thus, when the replacement medical device is placed into service, the user typically configures it with the most up-to-date user-specific configuration data.

However, relying on the user to update user-specific configuration data can be burdensome. Furthermore, the user may incorrectly update user-specific configuration data (e.g., perform an incorrect update procedure), may update the user-specific configuration data with incorrect data, or may forget or fail to update user-specific configuration data on the replacement device.

This disclosure describes example techniques related to automatically configuring a replacement device with the most up-to-date user-specific configuration data. More specifically, when an in-use device is being replaced, the example techniques may be used to replace or update user-specific configuration data on the replacement device. For example, the in-use device may automatically transfer some or all of its user-specific configuration data to cause updating of outdated configuration data on the replacement device. Advantageously, automatically configuring a replacement device with the most up-to-date user-specific configuration data enables a substantially seamless handoff between devices.

Automatic configuration of a replacement device can be achieved in a variety of ways. The following describes examples in the context of medical devices. More specifically, one medical device corresponds to an in-use device, and another medical device corresponds to a replacement device.

In some examples, a replacement device (e.g., a first medical device) may be a wearable device configured to automatically detect whether it is being placed into service (e.g., deployed on the body of a user or otherwise prepared for use). Upon detecting that it is being placed into service, the replacement device may communicate with an in-use device (e.g., a second medical device) to obtain the most up-to-date configuration data. When the replacement device obtains the configuration data from the in-use device, the configuration data may be used to automatically configure the replacement device.

There are a variety of ways in which the replacement device can detect that it is being placed into service. For example, the replacement device may detect activation of its cannula insertion mechanism, process a sensor signal indicative of skin contact, detect actuation of a mechanical switch located on a surface of the replacement device, and/or determine that an integrated glucose sensor is in contact with interstitial fluid.

In some examples, an in-use device (e.g., a first medical device) may be a wearable device configured to automatically detect whether it is being taken out of service (e.g., removed from the body of a user or otherwise prepared for disuse). Upon detecting that it is being taken out of service, the in-use device may communicate with a replacement device (e.g., a second medical device) so that the replacement device obtains the most up-to-date configuration data. When the replacement device obtains the configuration data from the in-use device, the configuration data may be used to automatically configure the replacement device.

There are a variety of ways in which the in-use device can detect that it is being taken out of service. For example, the in-use device may determine that its cannula is no longer inserted in the body of the user, process a sensor signal indicative of an absence of skin contact, detect resetting of a mechanical switch located on a surface of the in-use device, and/or determine that an integrated glucose sensor is not in contact with interstitial fluid.

In some examples, a charger device (e.g., a docking station or a wireless charging mat) may be used to "trickle transfer" configuration data from an in-use device (e.g., a first medical device) to a replacement device (e.g., a second medical device). Thus, the charger device may be configured to communicate with one or more cloud-based servers to obtain configuration data as it is updated at the in-use device. In this way, the replacement device may be automatically configured with the most up-to-date configuration data whenever the in-use device updates its configuration data.

FIG. 1 is a block diagram illustrating an example glucose level management system comprising a tethered pump, in accordance with one or more examples described in this disclosure. FIG. 1 illustrates system 10A that includes insulin pump 14, tubing 16, infusion set 18, monitoring device 20 (e.g., a glucose level monitoring device comprising a glucose sensor), patient device 24, and cloud 26. Insulin pump 14 may be described as a tethered pump, because tubing 16 tethers insulin pump 14 to infusion set 18. Cloud 26 represents a local, wide area or global computing network including one or more servers 28A-28N ("one or more servers 28"). Each of one or more servers 28 may include one or more processors and memory. In some examples, the various components may determine changes to therapy based on determination of glucose level for monitoring device 20, and therefore system 10A may be referred to as glucose level management system 10A.

Patient 12 may be diabetic (e.g., Type 1 diabetic or Type 2 diabetic), and therefore, the glucose level in patient 12 may be controlled with delivery of supplemental insulin. For example, patient 12 may not produce sufficient insulin to control the glucose level or the amount of insulin that patient 12 produces may not be sufficient due to insulin resistance that patient 12 may have developed.

To receive the supplemental insulin, patient 12 may carry insulin pump 14 that couples to tubing 16 for delivery of insulin into patient 12. Infusion set 18 may connect to the skin of patient 12 and include a cannula to deliver insulin into patient 12. Monitoring device 20 may also be coupled to patient 12 to measure glucose level in patient 12. Insulin pump 14, tubing 16, infusion set 18, and monitoring device 20 may together form an insulin pump system. One example of the insulin pump system is the MINIMED™ 670G insulin pump system by MEDTRONIC MINIMED, INC. However, other examples of insulin pump systems may be used and the example techniques should not be considered limited to the MINIMED™ 670G insulin pump system. For example, the techniques described in this disclosure may be utilized in insulin pump systems that include wireless communication capabilities. However, the example techniques should not be considered limited to insulin pump systems with wireless communication capabilities, and other types of communication, such as wired communication, may be possible. In another example, insulin pump 14, tubing 16, infusion set 18, and/or monitoring device 20 may be contained in the same housing.

As described in more detail below, in some examples, rather than utilizing a tethered pump system comprising insulin pump 14, tubing 16, infusion set 18, and/or monitoring device 20, patient 12 may utilize a patch pump, such as insulin pump 30 illustrated in FIG. 2. Insulin pump 30 may be described as a patch pump, because it can be removably attached to patient 12 using a small piece of adhesive material worn on the skin. Instead of delivering insulin via tubing and an infusion set, insulin pump 30 may deliver insulin via a cannula extending directly from insulin pump 30. In some examples, a glucose sensor may also be integrated into insulin pump 30. In such examples, insulin pump 30 may be referred to as an all-in-one (AIO) insulin pump.

Referring back to FIG. 1, insulin pump 14 may be a small device that patient 12 can place in different locations. For instance, patient 12 may clip insulin pump 14 to the waistband of pants worn by patient 12. In some examples, to be discreet, patient 12 may place insulin pump 14 in a pocket. In general, insulin pump 14 can be worn in various places, and patient 12 may place insulin pump 14 in a location based on the particular clothes patient 12 is wearing.

To deliver insulin, insulin pump 14 may include one or more reservoirs (e.g., two reservoirs). In some examples, a reservoir may be included in a plastic cartridge that holds up to N units of insulin (e.g., up to 300 units of insulin) and that can be secured within insulin pump 14. In some examples, a reservoir may be integrated into insulin pump 14 such that the reservoir can be filled using a syringe. Insulin pump 14 may be a battery-powered device that is powered by replaceable and/or rechargeable batteries.

Tubing 16 may connect at a first end to a reservoir in insulin pump 14 and may connect at a second end to infusion set 18. Tubing 16 may carry the insulin from the reservoir of insulin pump 14 to patient 12. Tubing 16 may be flexible, allowing for looping or bends to minimize concern of tubing 16 becoming detached from insulin pump 14 or infusion set 18 or concern from tubing 16 breaking.

Infusion set 18 may include a thin cannula that patient 12 inserts into a layer of fat under the skin (e.g., subcutaneous connection). Infusion set 18 may rest near the stomach of patient 12. The insulin may travel from the reservoir of insulin pump 14, through tubing 16, through the cannula in infusion set 18, and into patient 12. In some examples, patient 12 may utilize an infusion set insertion device. Patient 12 may place infusion set 18 into the infusion set insertion device, and with a push of a button on the infusion set insertion device, the infusion set insertion device may insert the cannula of infusion set 18 into the layer of fat of patient 12, and infusion set 18 may rest on top of the skin of the patient with the cannula inserted into the layer of fat of patient 12.

Monitoring device 20 may include a sensor that is inserted under the skin of patient 12, such as near the stomach of patient 12 or in the arm of patient 12 (e.g., subcutaneous connection). The sensor of monitoring device 20 may be configured to measure the interstitial glucose level, which is the glucose found in the fluid between the cells of patient 12. Monitoring device 20 may be configured to continuously or periodically sample the glucose level and rate of change of the glucose level over time.

In one or more examples, insulin pump 14, monitoring device 20, and/or the various components illustrated in FIG. 1, may together form a closed-loop therapy delivery system. For example, patient 12 may set a target glucose level, usually measured in units of milligrams per deciliter, on insulin pump 14. Insulin pump 14 may receive the current glucose level from monitoring device 20 and, in response, may increase or decrease the amount of insulin delivered to patient 12. For example, if the current glucose level is higher than the target glucose level, insulin pump 14 may increase the insulin. If the current glucose level is lower than the target glucose level, insulin pump 14 may temporarily cease delivery of the insulin. Insulin pump 14 may be considered as an example of an automated insulin delivery (AID) device. Other examples of AID devices may be possible, and the techniques described in this disclosure may be applicable to other AID devices. As described in more detail below, insulin pump 14 may be configured to operate in accordance with user-specific configuration data to delivery insulin to patient 12.

Insulin pump 14 and monitoring device 20 may be configured to operate together to mimic some of the ways in which a healthy pancreas works. Insulin pump 14 may be configured to deliver basal dosages, which are small amounts of insulin released continuously throughout the day. There may be times when glucose levels increase, such as due to eating or some other activity that patient 12 undertakes. Insulin pump 14 may be configured to deliver bolus dosages on demand in association with food intake or to correct an undesirably high glucose level in the bloodstream. In one or more examples, if the glucose level rises above a target level, then insulin pump 14 may deliver a bolus dosage to address the increase in glucose level. Insulin pump 14 may be configured to compute basal and bolus dosages and deliver the basal and bolus dosages accordingly. For instance, insulin pump 14 may determine the amount of a basal dosage to deliver continuously and then determine the amount of a bolus dosage to deliver to reduce glucose level in response to an increase in glucose level due to eating or some other event.

Accordingly, in some examples, monitoring device 20 may sample glucose levels for determining rate of change in glucose level over time. Monitoring device 20 may output the glucose level to insulin pump 14 (e.g., through a wireless link connection like Bluetooth or BLE). Insulin pump 14 may compare the glucose level to a target glucose level (e.g., as set by patient 12 or a clinician) and adjust the insulin dosage based on the comparison. In some examples, insulin pump 14 may adjust insulin delivery based on a predicted glucose level (e.g., where glucose level is expected to be in the next 30 minutes).

As described above, patient 12 or a clinician may set one or more target glucose levels on insulin pump 14. There may be various ways in which patient 12 or the clinician may set a target glucose level on insulin pump 14. As one example, patient 12 or the clinician may utilize patient device 24 to communicate with insulin pump 14. Examples of patient device 24 include mobile devices, such as smartphones, tablet computers, laptop computers, and the like. In some examples, patient device 24 may be a special programmer or controller (e.g., a dedicated remote control device) for insulin pump 14. Although FIG. 1 illustrates one patient device 24, in some examples, there may be a plurality of patient devices. For instance, system 10A may include a mobile device and a dedicated wireless controller, each of which is an example of patient device 24. For ease of description only, the example techniques are described with respect to patient device 24 with the understanding that patient device 24 may be one or more patient devices.

Patient device 24 may also be configured to interface with monitoring device 20. As one example, patient device 24 may receive information from monitoring device 20 through insulin pump 14, where insulin pump 14 relays the information between patient device 24 and monitoring device 20. As another example, patient device 24 may receive information (e.g., glucose level or rate of change of glucose level) directly from monitoring device 20 (e.g., through a wireless link).

In one or more examples, patient device 24 may comprise a user interface with which patient 12 or the clinician may control insulin pump 14. For example, patient device 24 may comprise a touchscreen that allows patient 12 or the clinician to enter a target glucose level. Additionally or alternatively, patient device 24 may comprise a display device that outputs the current and/or past glucose level. In some examples, patient device 24 may output notifications to patient 12, such as notifications if the glucose level is too high or too low, as well as notifications regarding any action that patient 12 needs to take. For example, if the batteries of insulin pump 14 are low on charge, then insulin pump 14 may output a low battery indication to patient device 24, and patient device 24 may in turn output a notification to patient 12 to replace or recharge the batteries.

Controlling insulin pump 14 through a display device of patient device 24 is merely provided as an example and should not be considered limiting. For example, insulin pump 14 may include pushbuttons that allow patient 12 or the clinician to set the various glucose levels of insulin pump 14. In some examples, insulin pump 14 itself, or in addition to patient device 24, may be configured to output notifications to patient 12. For instance, if the glucose level is too high or too low, insulin pump 14 may output an audible or haptic output. In some examples, if the battery is low, then insulin pump 14 may output a low battery indication on a display of insulin pump 14.

In the example of FIG. 1, insulin pump 14 may be an in-use device or a replacement device. In some examples, the replacement insulin pump may be similar, including identical, to insulin pump 14 (e.g., same make and model with same capabilities). However, in some other examples, the replacement insulin pump may not be similar (e.g., have different capabilities) to insulin pump 14.

As described above, during the operation of insulin pump 14, user-specific configuration data may be updated. Examples of user-specific configuration data include one or more insulin delivery rate limits (e.g., a maximum basal rate and/or a maximum bolus rate), insulin-on-board (e.g., unmetabolized insulin from one or more previous bolus dosages), a history of insulin delivery, one or more glucose sensor calibration factors (e.g., a previous and/or current sensor sensitivity ratio for converting a sensor signal value into a blood glucose level), a safe basal rate (e.g., a basal rate that is fixed in that it does not adjust based on current sensor values), and an insulin sensitivity factor (e.g., a ratio that describes the effect of one unit of insulin on glucose levels). It should be appreciated that the above are non-limiting examples of user-specific configuration data stored on insulin pump 14 and that the particular configuration data used may vary from implementation to implementation.

When insulin pump 14 is replaced (e.g., rotated, swapped out), a replacement insulin pump may not have the updated user-specific configuration data. To address this problem, disclosed herein are example techniques for automating the transfer of user-specific configuration data from an in-use device (e.g., insulin pump 14) to a replacement device (e.g., a replacement insulin pump). In some examples, user-specific configuration data may be transferred when the in-use device is being taken out of service and/or the replacement device is being placed into service. For instance, the in-use device may transfer the user-specific configuration data in response to a determination that the in-use device is being removed from service. Additionally or alternatively, the replacement device may request the user-specific configuration data in response to a determination that the replacement device is being placed into service.

Waiting to transfer user-specific configuration data when the in-use device is being taken out of service and/or is being placed into service increases the likelihood that the replacement device will receive the most up-to-date user-specific configuration data. Furthermore, when the transfer of the user-specific configuration data is automated, little to no patient interaction may be involved. Relying on patient 12 or some other user to configure the replacement device can introduce human error. By automating, such human error may be minimized or avoided altogether.

User-specific configuration data can be transferred between an in-use device and a replacement device in a variety of ways. As one example, the in-use device may directly communicate (e.g., via push or pull) the user-specific configuration data to the replacement device. As another example, the in-use device may indirectly communicate the user-specific configuration data to the replacement device via an intermediate device (e.g., patient device 24 or one or more servers 28 of cloud 26). Furthermore, user-specific configuration data may be transferred via any number of various communication links (e.g., radio frequency (RF) communication, Bluetooth (BLE) communication, near-field communication (NFC), or optical communication).

As illustrated in FIG. 1, system 10A includes cloud 26 that includes one or more servers 28. Cloud 26 may include a plurality of network devices (e.g., servers 28), and each network device may include one or more processors. Cloud 26 represents a cloud infrastructure that supports one or more servers 28 which may execute applications or operations requested by one or more users. For example, one or more servers 28 may remotely store, manage, and/or process data that would otherwise be locally stored, managed, and/or processed by patient device 24. One or more processors of one or more servers 28 may share data or resources for performing computations and may be part of computing servers, web servers, database servers, and the like. One or more servers 28 may be within a data center or may be distributed across multiple data centers. In some cases, the data centers may be in different geographical locations.

One or more processors of one or more servers 28, as well as other processing circuitry described herein, can include one or more of any of the following: microprocessors, digital signal processors (DSPs), application specific integrated circuits (ASICs), field programmable gate arrays (FPGAs), or any other equivalent integrated or discrete logic circuitry, as well as any combinations of such components. The functions attributed to the one or more processors, as well as other processing circuitry described herein may be embodied as hardware, firmware, software or any combination thereof.

One or more processors of one or more servers 28 may be implemented as fixed-function circuits, programmable circuits, or a combination thereof. Fixed-function circuits refer to circuits that provide particular functionality and are preset on the operations that can be performed. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of processors may include distinct circuit blocks (fixed-function or programmable), and in some examples, the one or more processors may include integrated circuits. The one or more processors may include arithmetic logic units (ALUs), elementary function units (EFUs), digital circuits, analog circuits, and/or programmable cores, formed from programmable circuits. In examples where the operations of one or more servers 28 are performed using software executed by the programmable circuits, memory accessible by one or more servers 28 may store the object code of the software that one or more processors of one or more servers 28 receive and execute.

Figure 2:
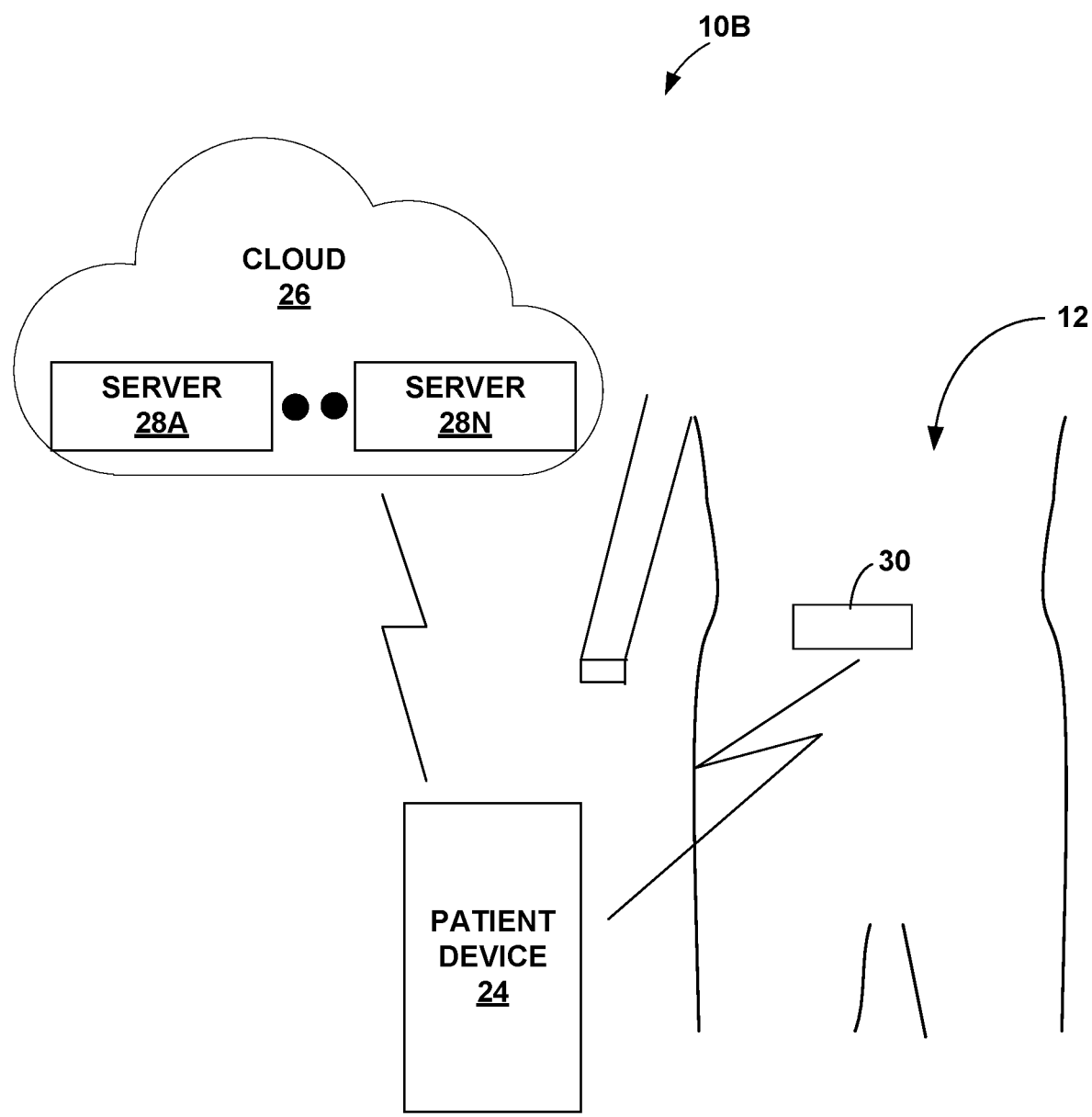
FIG. 2 is a block diagram illustrating an example glucose level management system comprising a patch pump, in accordance with one or more examples described in this disclosure.

FIG. 2 is a block diagram illustrating an example glucose level management system comprising a patch pump, in accordance with one or more examples described in this disclosure. FIG. 2 illustrates system 10B that is similar to system 10A of FIG. 1. However, in system 10B, patient 12 may not have insulin pump 14. Rather, patient 12 may utilize insulin pump 30 to deliver insulin.

Insulin pump 30 may be different than insulin pump 14 in that insulin pump 30 is an example of an on-body pump. Stated differently, insulin pump 30 is designed to be removably affixed to the skin of patient 12.

In one or more examples, insulin pump 30 may include a glucose sensor similar to that of monitoring device 20. Having the glucose sensor integrated into insulin pump 30 may be beneficial because of reduction in device on-body footprint, more reliable communication between the glucose sensor and components of insulin pump 30 (e.g., having a wired instead of wireless connection between the glucose sensor and the components of insulin pump 30), and sharing of components such as the same processing circuitry for the pump and the glucose sensor, as a few examples. Insulin pump 30 may be referred to as an all-in-one (AIO) insulin pump. In some other examples, rather than the glucose sensor being integrated into insulin pump 30, the glucose sensor may included in a device (e.g., monitoring device 20) that is separate from insulin pump 30.

Patient 12 may replace insulin pump 30, for example, when the battery of insulin pump 30 is nearly depleted, when the insulin reservoir of insulin pump 30 is empty, or when the cannula of insulin pump 30 becomes occluded. In some examples, patient 12 may replace insulin pump 30 every few days (e.g., every 3 days).

In some examples, insulin pump 30 may be fully disposable in that patient 12 replaces insulin pump 30 in its entirety with a new insulin pump. However, in some other examples, insulin pump 30 may be semi-disposable in that it includes a durable/reusable portion and a consumable/disposable portion.

Figure 3A:
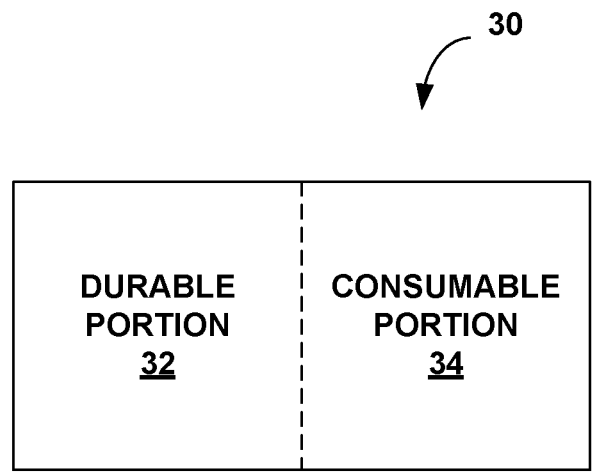
FIGS. 3A and 3B are different perspective views of a semi-disposable patch pump configured to provide therapy, in accordance with one or more examples described in this disclosure.
Figure 3B:
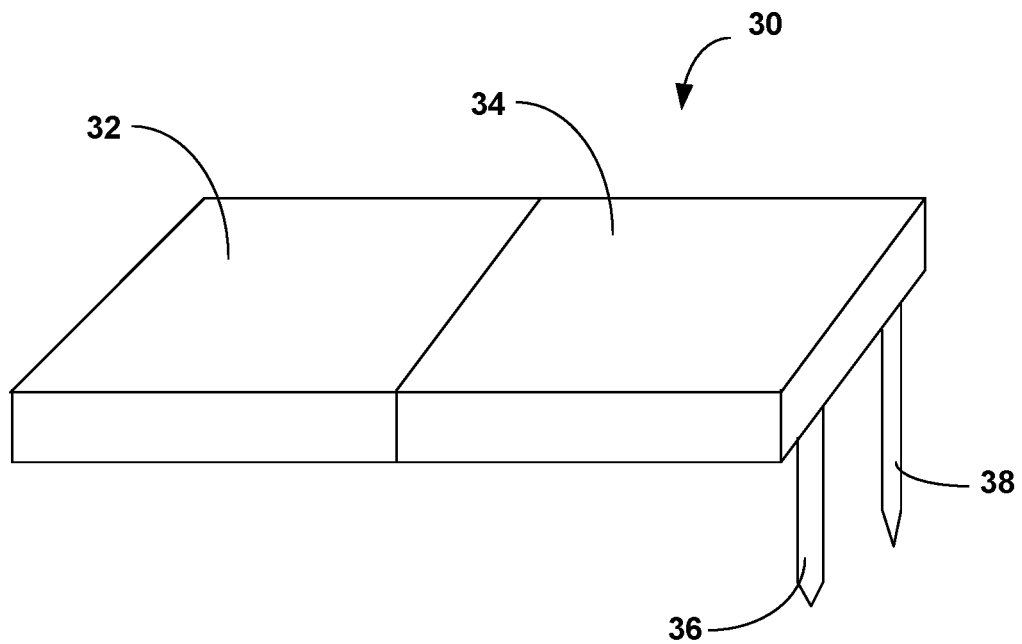

For example, FIGS. 3A and 3B are different perspective views of a semi-disposable patch pump configured to provide therapy, in accordance with one or more examples described in this disclosure. FIG. 3A illustrates durable portion 32 and consumable portion 34 of insulin pump 30. In some examples, durable portion 32 includes electronics (e.g., rechargeable batteries, processor, and memory), and consumable portion 34 includes insulin-contacting components, such as an insulin reservoir. As illustrated in FIG. 3B, consumable portion 34 may also include patient-contacting components, such as cannula 36 and glucose sensor 38. Glucose sensor 38 may be similar to the glucose sensor of monitoring device 20.

There are a variety of ways in which durable portion 32 and consumable portion 34 may be operatively coupled. For example, there may be an electrical connection that facilitates communication between a processor of portion 32 and various components of portion 34, a mechanical connection that enables a motor of portion 32 to exert a force on gears of portion 34, and/or an electromagnetic connection that allows a motor stator in portion 32 to induce movement of a motor rotor in portion 34.

Regardless of whether a patch pump is fully disposable or semi-disposable, it may be replaced periodically. For example, a semi-disposable patch pump may comprise a battery in a durable portion and a reservoir in a consumable portion. When the reservoir is empty, the patch pump may be removed from patient 12, and the durable portion may be separated from the consumable portion. Upon separation, the durable portion may have its battery recharged (e.g., by connecting the durable portion to a charger device), and the consumable portion may simply be discarded. A replacement patch pump may be formed based on removably securing a replacement durable portion (e.g., a second durable portion that has recently been disconnected from the charger device) to a new consumable portion. Thus, patient 12 may have at least two durable portions—an in-use durable portion that is attached to patient 12 and a replacement durable portion that stands by waiting to replace the in-use durable portion.

However an in-use device and a replacement device may have different data stored in memory. For example, an in-use durable portion may have the most up-to-date configuration data, whereas a replacement durable portion may have default configuration data. A user may manually configure the replacement durable portion with the most up-to-date configuration data, but this approach tends to be error-prone. Furthermore, a manual configuration process may be so time-consuming that some data becomes outdated before the process can be completed. To address this problem, this disclosure describes example ways in which to automatically transfer user-specific configuration data between an in-use device and a replacement device.

Some example ways of automatically transferring user-specific configuration data involve a replacement device (e.g., a first medical device) that is configured to automatically determine whether it is being placed into service (e.g., placed in contact with the body of a user or otherwise prepared for use). The replacement device may be a replacement for an in-use device (e.g., a second medical device that was previously placed into service to provide medical therapy to patient 12 in accordance with user-specific configuration data stored on the second medical device). Upon determining that it is being placed into service, the replacement device may automatically communicate data indicative of the replacement device being placed into service (e.g., a request for the user-specific configuration data). Thereafter, the replacement device may obtain the user-specific configuration data, and the replacement device may be automatically configured to provide therapy in accordance with the user-specific configuration data.

There are a variety of ways in which the replacement device may determine that it is being placed into service. For example, in the context of a semi-disposable patch pump, durable portion 32 may determine that it has been removably attached to consumable portion 34 (e.g., based on a signal from a magnetoresistive (MR) sensor, a mechanical switch, a light sensor, and/or a Hall sensor configured to detect a motor rotor in consumable portion 34) in preparation for deployment on the body of patient 12. Provided below are some other examples that are not necessarily limited to the context of a semi-disposable patch pump.

In some examples, the replacement device may determine it is being placed into service based on determining activation of a cannula insertion mechanism associated with the replacement device. For example, the cannula insertion mechanism may comprise conductive elements configured to interface with conductive elements on the pump housing upon cannula insertion, thereby completing a circuit for conveying an electrical signal to a processor.

In some examples, the replacement device may determine it is being placed into service based on processing an electrical signal from a skin contact sensor (e.g., a temperature sensor, a sweat sensor, a bioimpedance sensor, a capacitance sensor, and/or an optical sensor) associated with the replacement device. For example, durable portion 32 may include a pulse oximeter configured to detect a heart rate that can be used to determine that durable portion 32 has been deployed on the body of patient 12.

In some examples, the replacement device may determine it is being placed into service based on determining actuation of a mechanical switch (e.g., a snap action switch or a tactile switch). For example, durable portion 32 may include a mechanical switch configured to either complete or break a circuit upon actuation, which may result from contact with consumable portion 34 or the body of a user.

In some examples, the replacement device may determine it is being placed into service based on determining that a glucose sensor associated with the replacement device is in contact with interstitial fluid. For example, upon contact with interstitial fluid, a glucose sensor may generate an electrical signal that is communicated to a processor housed in durable portion 32.

In some examples, the replacement device may determine it is being placed into service based on accelerometer data indicative of placement on the body of a user. For example, durable portion 32 may include an accelerometer configured to generate signals that can be processed to determine movement that is consistent with walking and/or to synthesize a biometric profile (e.g., based on a user's gait).

In some examples, the replacement device may determine it is being placed into service based on processing a signal indicative of a pull tab being removed from the replacement device. For example, a plastic pull tab may isolate a battery from a circuit such that removal of the pull tab may close the circuit, thereby enabling an electrical signal to be conveyed along the circuit to a processor.

In some examples, the replacement device may determine it is being placed into service based on determining that a charger device has been disconnected from the replacement device. For example, a replacement device may detect the absence of power being supplied to its battery.

In some examples, the replacement device may determine it is being placed into service based on receiving user input. For example, a replacement device may have one or more buttons which, when pressed by patient 12, causes the replacement device to wake up, establish a communication link with another device (e.g., an in-use device or an intermediate device), and/or communicate directly/indirectly with an in-use device.

In some examples, the replacement device may determine it is being placed into service based on establishing a communication link with another device. For example, a replacement device may determine that it is being placed into service when a network connection is formed with an in-use device or patient device 24.

Some example ways of automatically transferring user-specific configuration data involve an in-use device (e.g., a first medical device) that is configured to automatically determine whether it is being removed from service. The in-use device may have been previously placed into service to provide therapy in accordance with user-specific configuration data stored on the in-use device. Upon determining that the in-use device is being removed from service, a replacement device (e.g., a second medical device) may be configured to provide therapy in accordance with the user-specific configuration data. This may involve the in-use device communicating the user-specific configuration data toward the replacement device (e.g., directly or indirectly via one or more intermediate devices). For example, the in-use device may transmit the user-specific configuration data to the replacement device, thereby causing the replacement device to configure itself to provide therapy in accordance with the user-specific configuration data.

There are various ways in which the in-use device may determine it is being removed from service. For example, in the context of a semi-disposable patch pump, durable portion 32 may determine that it has been separated from consumable portion 34 (e.g., based on a signal/the absence of a signal from a MR sensor, a mechanical switch, a light sensor, and/or a Hall sensor configured to detect a motor rotor in consumable portion 34) after removal from patient 12. Provided below are some other examples that are not necessarily limited to the context of a semi-disposable patch pump.

In some examples, the in-use device may determine it is being removed from service based on determining removal of a cannula from the body of a user. For example, cannula removal may cause a decrease in pumping back-pressure, which may be detected by a force sensor configured to measure reaction force on a reservoir plunger.

In some examples, the in-use device may determine it is being removed from service based on processing a signal from a skin contact sensor associated with the in-use device. For example, durable portion 32 may include a light sensor that fails to detect light when placed against the body of a user and that detects light when no longer placed against the body of the user.

In some examples, the in-use device may determine it is being removed from service based on detecting a reset of a mechanical switch. For example, durable portion 32 may include a mechanical switch configured to automatically reset when no longer in contact with (e.g., separated from) consumable portion 34 or the body of a user.

In some examples, the in-use device may determine it is being removed from service based on determining that a glucose sensor associated with the in-use device is no longer in contact with interstitial fluid. For example, a glucose sensor may periodically (e.g., every five minutes) generate an electrical signal when it is in contact with interstitial fluid, so the in-use device may determine that the absence of an expected signal is indicative of removal.

In some examples, the in-use device may determine it is being removed from service based on processing a signal indicative of removal of a pull tab situated between the in-use device and a user. For example, a conductive/magnetic pull tab may be adhered to patient 12 such that when in-use device is removed from patient 12, the pull tab breaks a circuit, thereby preventing an electrical signal from being conveyed along the circuit to a processor.

In some examples, the in-use device may determine it is being removed from service based on determining that a charger device has been connected to the in-use device. For example, the in-use device may detect power being supplied to its battery.

In some examples, the in-use device may determine it is being removed from service based on receiving user input. For example, an in-use device may have one or more buttons which, when pressed by patient 12, causes the in-use device to wake up, establish a communication link with another device (e.g., a replacement device or an intermediate device), and/or communicate directly/indirectly with a replacement device.

In some examples, the in-use device may determine it is being removed from service based on detecting that a component has become inoperable. For example, the in-use device may determine that it has a low battery, that it has an empty insulin reservoir, and/or that a glucose sensor has reached the end of its life based on processing a signal from a battery monitor, processing a signal from a force sensor, and/or failing to process any signal from the glucose sensor.

In some examples, the in-use device may determine it is being removed from service based on discontinuing communications with another device. For example, an in-use device may determine it is being removed from service when it loses a network connection with a replacement device or patient device 24.

For the avoidance of doubt, it is further emphasized that the example techniques disclosed herein are not limited to semi-disposable patch pumps but are equally applicable to various other devices, including medical devices (e.g., insulin pump 14 or monitoring device 20) and non-medical devices (e.g., a smartwatch or computing eyewear). For example, tubing 16 may include a magnet where it is configured to connect with insulin pump 14. Thus, insulin pump 14 may determine that it is being put into service when the magnet is detected, and insulin pump 14 may determine that it is being removed from service when the magnet is no longer detected.

Some example ways of automatically transferring user-specific configuration data involve an intermediate device (e.g., patient device 24) that is configured to automatically determine whether a replacement device is being placed into service and/or an in-use device is being removed from service. For example, patient device 24 may determine received signal strength indication (RSSI) values for signals received from an in-use medical device and a replacement medical device that are each communicatively coupled to patient device 24. Each RSSI value may be indicative of a distance between patient device 24 and a respective device. Typically, the in-use medical device and patient device 24 are located on or near patient 12. Thus, patient device 24 may identify the in-use medical device based on associating it with a consistently high RSSI value. Furthermore, patient device 24 may use RSSI values to determine that the in-use medical device is being removed from service and that the replacement medical device is being placed into service and vice versa.

Figure 4:
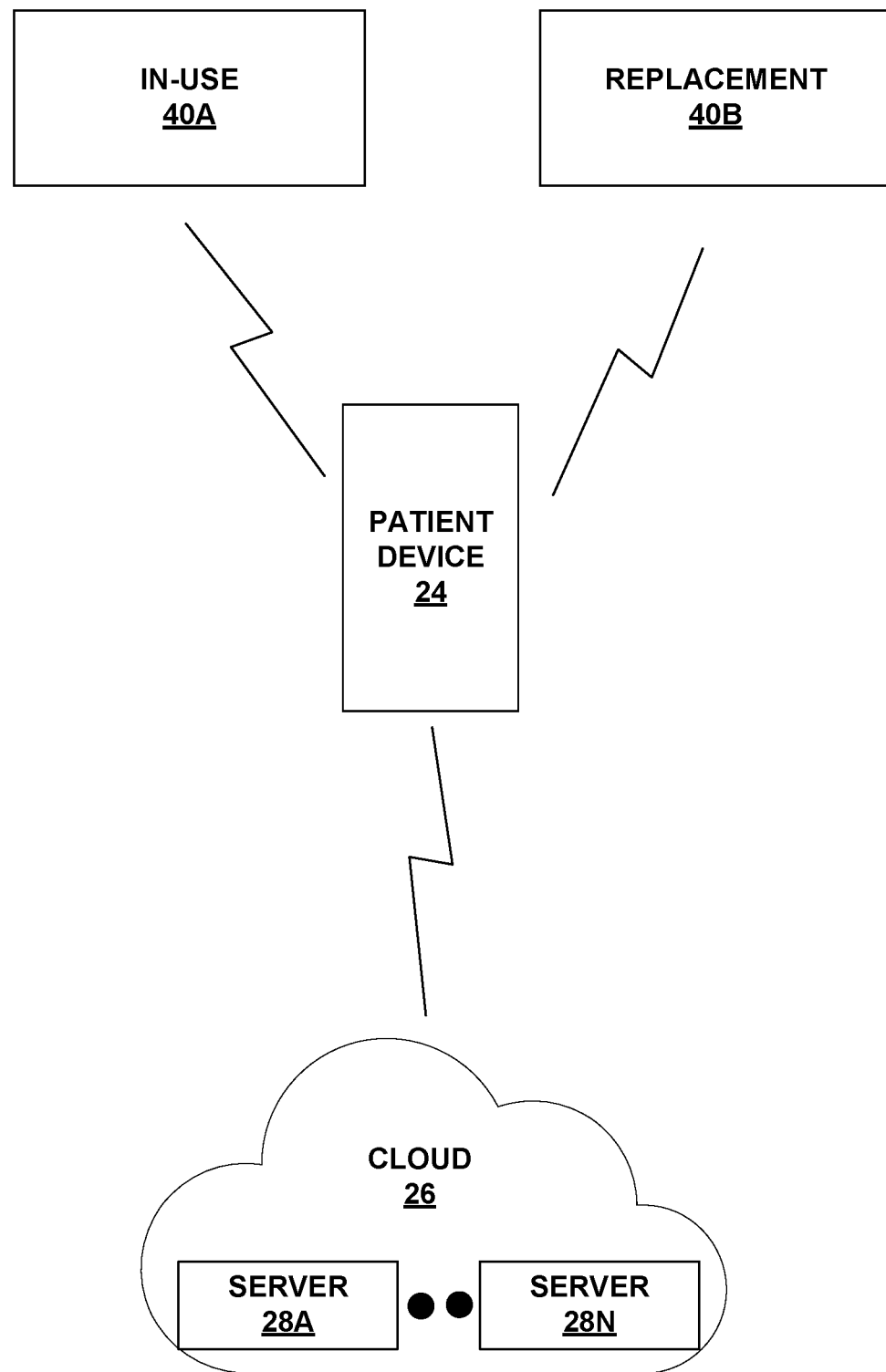
FIG. 4 is a block diagram illustrating an example communication system for transferring user-specific configuration data via an intermediate device, in accordance with one or more examples described in this disclosure.

FIG. 4 is a block diagram illustrating an example communication system for transferring user-specific configuration data via an intermediate device, in accordance with one or more examples described in this disclosure. FIG. 4 illustrates in-use medical device 40A and replacement medical device 40B communicating with patient device 24. Optionally, patient device 24 may be communicatively coupled to one or more servers 28 of cloud 26.

When user-specific configuration data is updated, device 40A may communicate the updated configuration data to patient device 24. Communication of the updated configuration data may be achieved in a variety of ways. For example, device 40A may transmit the updated configuration data to patient device 24 in response to determining that user-specific configuration data has been updated. As another example, patient device 24 may periodically poll device 40A to determine whether it has any updated configuration data, and if so, patient device 24 may request the updated configuration data.

In some examples, patient device 24 may store the updated configuration data in its memory. For example, patient device 24 may cache the updated configuration data. In some examples, patient device 24 may communicate the updated configuration data to another device without keeping a copy on patient device 24. For example, patient device 24 may stream the updated configuration data to cloud 26. In some examples, patient device 24 may communicate the updated configuration data to cloud 26, and one or more servers 28 of cloud 26 may store the updated configuration data. For example, the updated configuration data may be transferred (e.g., via push and/or pull) between patient device 24 and a database in cloud 26 that stores the updated configuration data.

When device 40B is being placed into service and/or when device 40A is being removed from service, patient device 24 may determine whether it has the most up-to-date configuration data. For example, when device 40B is being placed into service, patient device 24 may request configuration data from device 40A (e.g., in response to receiving a request for configuration data from device 40B, upon establishing a communication link with device 40B, or otherwise based on determining that device 40B is being placed into service). Additionally or alternatively, in response to determining that device 40A is being removed from service, device 40A may transmit its configuration data to patient device 24. Upon obtaining the configuration data from device 40A, patient device 24 may determine whether the obtained configuration data is an updated version of configuration data stored on patient device 24 (e.g., by comparing the obtained configuration data to configuration data stored on patient device 24 and/or obtained from cloud 26). When patient device 24 determines that the obtained configuration data is an updated version, patient device 24 may update its outdated configuration data.

Patient device 24 may communicate the most up-to-date configuration data to device 40B for automatic configuration. In some examples, this may involve transfer of the configuration data over a previously established communication link between patient device 24 and device 40B. In some other examples, this may involve establishing a communication link between patient device 24 and device 40B.

In some examples, user-specific configuration data may be automatically transferred based on predicting when device replacement will occur. For example, a history of device replacement may be collected, and machine learning techniques may be applied to the history to determine one or more patterns, which can be used to predict when device replacement will occur. Based on such predictions, device 40A, device 40B, and/or patient device 24 may automatically initiate transfer of user-specific configuration data.

As mentioned above, transfer of user-specific configuration data may be automatically initiated by one or more devices (e.g., device 24, device 40A, and/or device 40B).

However, in some examples, transfer of user-specific configuration data may be initiated based on user input. For example, patient 12 may press one or more buttons (e.g., in a prescribed sequence of presses) on device 40A, device 40B, and/or device 24 to initiate transfer of user-specific configuration data between device 40A and device 40B. Pressing the one or more buttons may cause one or more devices to wake up, establish one or more communication links for transferring user-specific configuration data, and/or communicate over the one or more communication links.

In some examples, user-specific configuration data may be transferred based on user intervention. For example, user-specific configuration data may be stored on a memory card (e.g., subscriber identification module (SIM) card or micro secure digital (SD) card) or some other removable data storage medium. Thus, patient 12 may physically transfer the memory card from device 40A to device 40B (and vice versa) to facilitate automatic configuration based on the content of the memory card.

Figure 5:
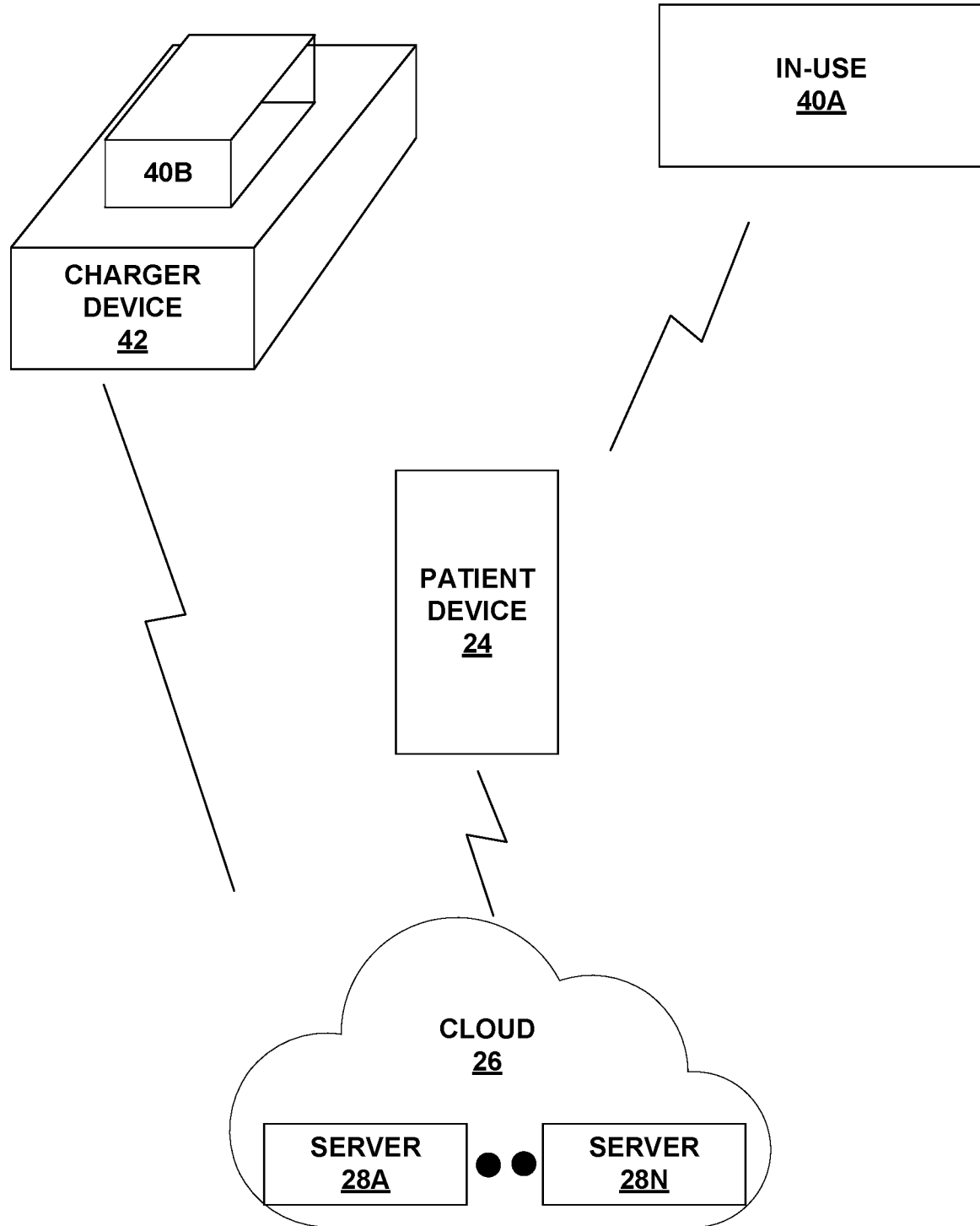
FIG. 5 is a block diagram illustrating an example communication system comprising a networked charger device, in accordance with one or more examples described in this disclosure.

FIG. 5 is a block diagram illustrating an example communication system comprising a networked charger device, in accordance with one or more examples described in this disclosure. In some examples, rather than or in addition to transferring user-specific configuration data when an in-use device is being removed from service and/or a replacement device is being placed into service, user-specific configuration data may be "trickle" transferred between the in-use device and the replacement device. This may involve a network of one or more intermediate devices (e.g., patient device 24, charger device 42, and/or one or more servers 28 of cloud 26). For instance, when user-specific configuration data is updated, the in-use device may communicate the updated user-specific configuration data to an intermediate device (e.g., patient device 24 which communicates the updated user-specific configuration data to one or more servers 28 of cloud 26), and the replacement device may synchronize its version of user-specific configuration data with the version available on an intermediate device (e.g., charger device 42 which obtains the updated user-specific configuration data from one or more servers 28 of cloud 26).

In some examples, when in-use device 40A is in service, the batteries of replacement device 40B may be charged. As illustrated in FIG. 5, charger device 42 may be configured to charge the batteries of replacement device 40B. Charger device 42 may be connected to a power source, such as AC power in a home via a wall socket.

Charger device 42 may be configured to utilize any of a variety of techniques to charge the batteries of replacement device 40B. In some examples, charger device 42 may be configured to charge replacement device 40B via an electrical connection (e.g., conductive contacts or a power cable that plugs into replacement device 40B). In some other examples, charger device 42 may be configured to wirelessly charge the batteries of replacement device 40B. For example, charger device 42 may include an induction coil to create an alternating electromagnetic field, and replacement device 40B may include a receiver coil that converts the electromagnetic filed into electricity that is fed to the battery for charging.

In the example of FIG. 5, charger device 42 may be configured to communicate data to replacement device 40B. Data may be communicated at any time relative to power transmission (e.g., prior to, concurrently with, and/or subsequent to). In examples where charger device 42 outputs power to replacement device 40B through a power cable, the power cable may be a universal serial bus (USB) cable, such as a USB-C cable, that is also configured for data transfer.

In examples where charger device 42 outputs power wirelessly, charger device 42 may utilize near field communication (NFC) techniques for communicating with replacement device 40B.

Various communication protocols may be used to transfer data between charger device 42 and replacement device 40B. In some examples, data transfer may occur upon determining that an updated version of configuration data is available. For example, charger device 42 may be configured to push configuration data to replacement device 40B in response to determining that the configuration data is an updated version (e.g., based on comparing configuration data obtained from cloud 26 against configuration data stored on charger device 42). As another example, replacement device 40B may be configured to pull configuration data from charger device 42 (e.g., based on periodically polling charger device 42 for updated configuration data). In some other examples, data transfer may occur irrespective of whether an updated version of configuration data is available. For example, charger device 42 may periodically (e.g., at predetermined time intervals) or continuously push user-specific configuration information to replacement device 40B. As another example, replacement device 40B may periodically or continuously pull user-specific configuration data from charger device 42. Regardless of the manner in which it is performed, the data transfer may cause automatic configuration of replacement device 40B with updates.

As mentioned above, charger device 42 may obtain configuration data from cloud 26. Data transfer between charger device 42 and cloud 26 may be performed using various communication protocols (e.g., push or pull) and with or without determining whether an updated version of configuration data is available. For example, charger device 42 may periodically poll one or more servers 28 of cloud 26 for any updated configuration data. In response to receiving a request for any updated configuration data, one or more servers 28 may determine whether it has an updated version of configuration data on charger device 42 (e.g., based on comparing a timestamp in the request to a timestamp for configuration data stored on one or more servers 28). When one or more servers 28 determines that it has an updated version, it may communicate all or part of the updated version (e.g., based on comparing different versions to determine which portion of configuration data has changed) to charger device 42.

In one or more examples, in-use device 40A may communicate user-specific configuration data toward one or more servers 28 (e.g., directly to or indirectly via patient device 24). Data transfer between in-use device 40A and one or more servers 28 may be performed using various communication protocols (e.g., push or pull) and with or without determining whether an updated version of configuration data is available. For instance, whenever its user-specific configuration data is updated, in-use device 40A may push the updated user-specific configuration data to patient device 24 or one or more servers 28.

In examples involving patient device 24 as an intermediate device between in-use device 40A and one or more servers 28, data transfer between patient device 24 and one or more servers 28 may also be performed using various communication protocols (e.g., push or pull) and with or without determining whether an updated version of configuration data is available. For example, patient device 24 may periodically communicate configuration data to one or more servers 28, which determines whether the configuration data obtained from patient device 24 is an updated version of configuration data stored on one or more servers 28 (e.g., based on comparing timestamps, checksums, or other metadata).

Using the example system of FIG. 5, in some instances, replacement device 40B may already have the most up-to-date user-specific configuration data by the time it is to be placed into service. However, to help ensure that replacement device 40B has the most up-to-date user-specific configuration data when it is being placed into service, one or more checks may be performed for any updated configuration data when device 40A is being removed from service and/or device 40B is being placed into service. For example, replacement device 40B may perform a check based on requesting configuration data from charger device 42 when device 40A is being removed from service and/or device 40B is being placed into service. Additionally or alternatively, replacement device 40B may perform a check based on requesting configuration data from patient device 24 when device 40A is being removed from service and/or device 40B is being placed into service. Performing multiple checks involving different devices may help account for network latency and/or connectivity issues that could hinder communication of updated configuration data to replacement device 40B.

Although the previous example is provided in terms of replacement device 40B requesting configuration data, it should be appreciated that the one or more checks may be performed with one or more other devices (alone or in combination with device 40B) using various communication protocols (e.g., push or pull) and with or without determining whether an updated version of configuration data is available. For example, when device 40A is being removed from service and/or device 40B is being placed into service, patient device 24 may establish a communication link with device 40B and push configuration data to it.

As mentioned above, one or more checks may be performed when device 40A is being removed from service and/or device 40B is being placed into service. In some examples, the one or more checks may be initiated upon detecting that device 40A is being removed from service and/or that device 40B is being placed into service. The detection may be performed using any number of the various techniques disclosed herein. For example, in-use device 40A may detect that it is being removed from service and communicate data indicative of removal to patient device 24, which may communicate the data to device 40B, thereby causing one or more checks to be performed.

Although the example of FIG. 5 involves a networked charger device 42, user-specific configuration data may be transferred via a charger device that is not networked. For instance, such a charger device may include two charging ports—one for device 40A and one for device 40B. When devices 40A and 40B are both in the charger device, patient 12 may press a button to initiate transfer of user-specific configuration data between devices 40A and 40B.

Figure 6:
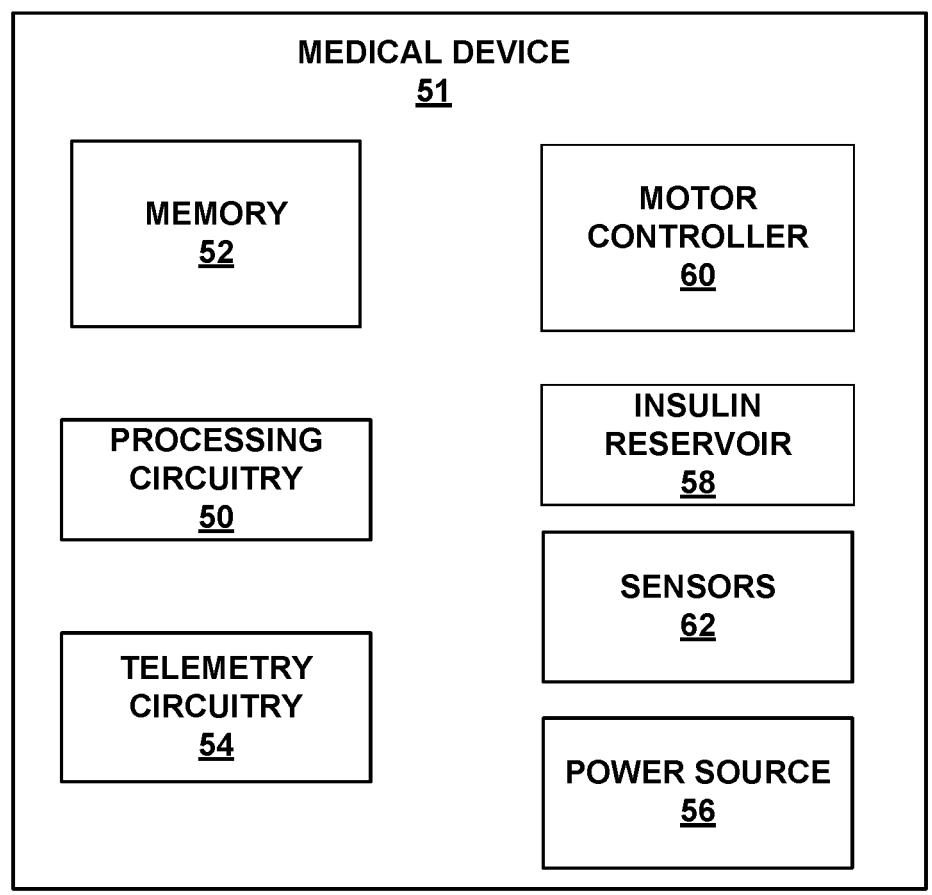
FIG. 6 is a block diagram illustrating an example medical device, in accordance with one or more examples described in this disclosure.

FIG. 6 is a block diagram illustrating an example medical device, in accordance with one or more examples described in this disclosure. FIG. 6 illustrates medical device 51, which may be an in-use device or a replacement device. Examples of medical device 51 include insulin pump 14 and insulin pump 30.

As illustrated, medical device 51 includes processing circuitry 50, memory 52, telemetry circuitry 54, power source 56, insulin reservoir 58, motor controller 60, and one or more sensors 62. Medical device 51 may include more or fewer components than those illustrated in FIG. 6. Also, when medical device 51 is a semi-disposable patch pump, some components of medical device 51 may be located in durable portion 32, and other components may be located in consumable portion 34. For example, processing circuitry 50, memory 52, telemetry circuitry 54, motor controller 60, sensors 62, and power source 56 may be part of durable portion 32; and insulin reservoir 58 may be part of consumable portion 34. However, the particular combination of components in durable portion 32 and consumable portion 34 may vary from implementation to implementation.

Memory 52 may store program instructions that, when executed by processing circuitry 50, cause processing circuitry 50 to provide the functionality ascribed to insulin pump 14, insulin pump 30, device 40A, and/or device 40B throughout this disclosure. Memory 52 may also store user-specific configuration data.

Memory 52 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 50 can take the form one or more microprocessors, DSPs, ASICs, FPGAs, programmable logic circuitry, or the like, and the functions attributed to processing circuitry 50 herein may be embodied as hardware, firmware, software or any combination thereof.

In one or more examples, processing circuitry 50 may utilize the user-specific configuration data stored in memory 52 to output instructions to motor controller 60 for regulating insulin delivery. Motor controller 60 may be configured to control the timing and amount of insulin displacement from insulin reservoir 58 based on the instructions from processing circuitry 50.

One or more sensors 62 may include a glucose sensor (e.g., glucose sensor 38) and/or any number of sensors capable of generating signals indicative of medical device 51 being placed into service and/or removed from service. For instance, one or more sensors 62 may include temperature sensors, sweat sensors, resistance sensors, and the like that are configured to generate signals indicative of whether or not medical device 51 is attached to the body of patient 12.

In accordance with one or more examples described in this disclosure, telemetry circuitry 54 may be configured to send and/or receive user-specific configuration data. Telemetry circuitry 54 may include any suitable hardware, firmware, software, or any combination thereof for enabling communication between medical device 51 and another device (e.g., one or more servers 28 of cloud 26, patient device 24, replacement device 40B, and/or charger device 42). Telemetry circuitry 54 may send and/or receive communications with the aid of an antenna, which may be internal and/or external to medical device 51. Telemetry circuitry 54 may be configured to communicate via wired or wireless communication techniques. Examples of local wireless communication techniques that may be employed to facilitate communication include RF communication according to IEEE 802.11, Bluetooth, or BLE specification sets, infrared communication, e.g., according to an IrDA standard, near field communication (NFC), or other standard or proprietary telemetry protocols. Telemetry circuitry 54 may also provide connectivity with a carrier network for access to cloud 26. In this manner, other devices may be capable of communicating with medical device 51.

Power source 56 delivers operating power to the components of medical device 51. In some examples, power source 56 may include a battery, such as a rechargeable or non-rechargeable battery. A non-rechargeable battery may last for several days or possibly longer, while a rechargeable battery may be periodically charged from an external device, e.g., on a daily or weekly basis, with charger device 42. Recharging of a rechargeable battery may be accomplished by using an alternating current (AC) outlet or through proximal inductive interaction between charger device 42 and an inductive charging coil within medical device 51. In some examples, the inductive charging coil may be the same as the coil used for communication by telemetry circuitry 54. In some other examples, the inductive charging coil may be separate from the coil used for communication by telemetry circuitry 54.

Figure 7:
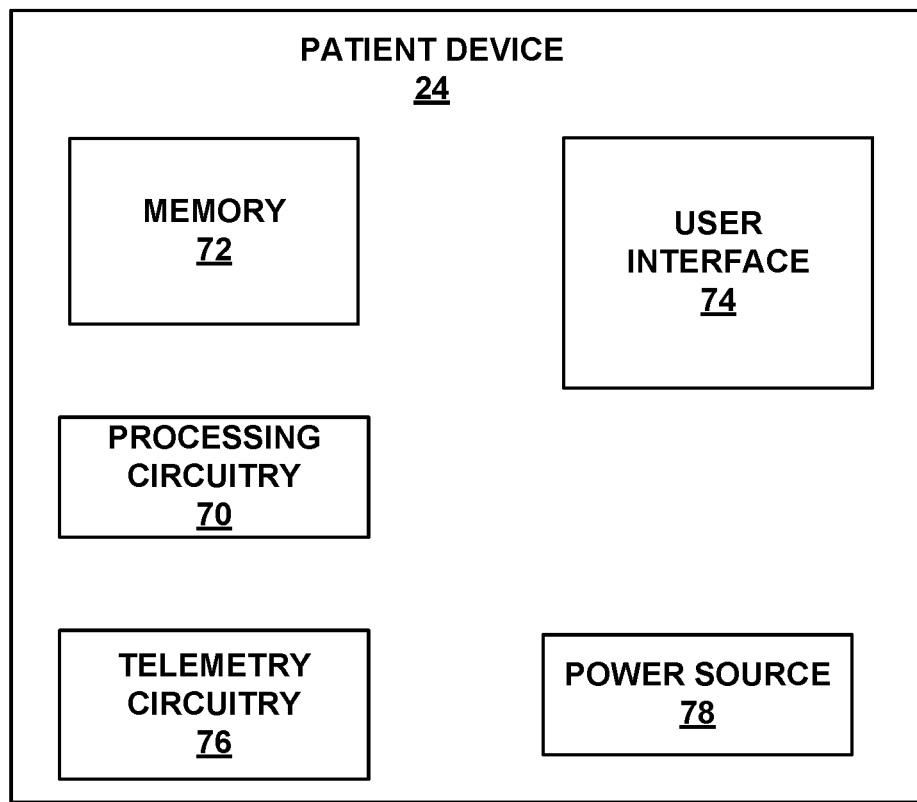
FIG. 7 is a block diagram illustrating an example of a patient device, in accordance with one or more examples described in this disclosure.

FIG. 7 is a block diagram illustrating an example of a patient device, in accordance with one or more examples described in this disclosure. While patient device 24 may generally be described as a hand-held computing device, in some examples, patient device 24 may be a notebook computer, a desktop computer, or a workstation, for example. In some examples, patient device 24 may be a mobile device, such as a smartphone or a tablet computer. Patient device 24 may execute an application that allows patient device 24 to perform example techniques described in this disclosure. In some examples, patient device 24 may be a specialized controller for communicating with medical device 51.

As illustrated in FIG. 7, patient device 24 may include processing circuitry 70, memory 72, user interface 74, telemetry circuitry 76, and power source 78. Memory 72 may store program instructions that, when executed by processing circuitry 70, cause processing circuitry 70 to provide the functionality ascribed to patient device 24 throughout this disclosure.

In some examples, memory 72 of patient device 24 may store user-specific configuration data. For example, in-use device 40A may transmit the user-specific configuration data to patient device 24, and memory 72 may store the user-specific configuration data for transmission to replacement device 40B, charger device 42, or one or more servers 28.

Memory 72 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 70 can take the form one or more microprocessors, DSPs, ASICs, FPGAs, programmable logic circuitry, or the like, and the functions attributed to processing circuitry 32 herein may be embodied as hardware, firmware, software, or any combination thereof.

User interface 74 may include a button or keypad, lights, a microphone for voice commands, and/or a display device, such as a liquid crystal (LCD). In some examples the display may be a touchscreen. Processing circuitry 70 may present and receive information relating to therapy via user interface 74. For example, processing circuitry 70 may receive user input via user interface 74. The user input may be entered, for example, by pressing a button on a keypad, entering text, or selecting an icon from a touchscreen. For example, to enter initial configuration data for medical device 51, patient 12 or a physician may utilize user interface 74 to enter the configuration data.

Telemetry circuitry 76 may include any suitable hardware, firmware, software, or any combination thereof for enabling communication between patient device 24 and another device, such as one or more servers 28 of cloud 26, in-use device 40A, replacement device 40B, and charger device 42. Telemetry circuitry 76 may send and/or receive communications with the aid of an antenna, which may be internal and/or external to patient device 24. Telemetry circuitry 76 may be configured to communicate via wired or wireless communication techniques. Examples of local wireless communication techniques that may be employed to facilitate communication between patient device 24 and another computing device include RF communication according to IEEE 802.11, Bluetooth, or BLE specification sets, infrared communication, e.g., according to an IrDA standard, near field communication (NFC), or other standard or proprietary telemetry protocols. Telemetry circuitry 76 may also provide connectivity with a carrier network for access to cloud 26. In this manner, other devices may be capable of communicating with patient device 24.

In some examples, telemetry circuitry 76 may include analog or digital RSSI detector circuitry that provides information indicative of the strength of signals received from different devices (e.g., in-use device 40A and replacement device 40B). As mentioned above, processing circuitry 70 may determine which device is in service and which device is out of service based on the information. In some examples, the information may also be indicative of signal quality (e.g., for how long the signal strength is high, how often the signal strength is high, and so forth).

Power source 78 delivers operating power to the components of patient device 24. In some examples, power source 39 may include a battery, such as a rechargeable or non-rechargeable battery. A non-rechargeable battery may last for several months or years, while a rechargeable battery may be periodically charged from an external device, e.g., on a daily or weekly basis. Recharging of a rechargeable battery may be accomplished by using an alternating current (AC) outlet or through proximal inductive interaction between an external charger and an inductive charging coil within patient device 24.

Figure 8:
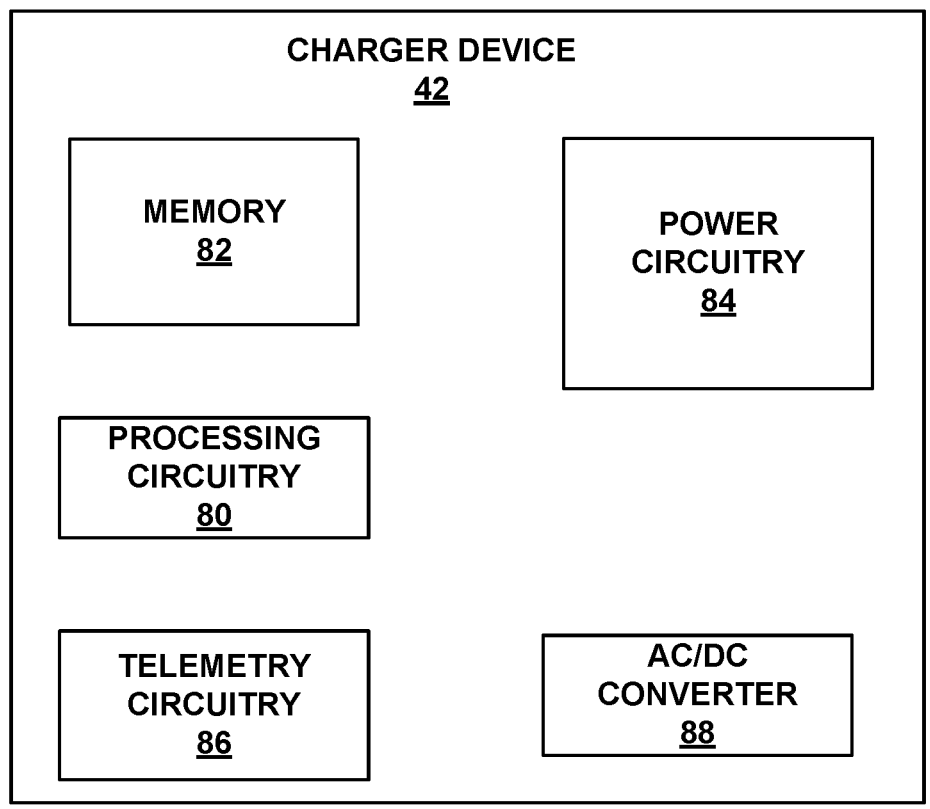
FIG. 8 is a block diagram illustrating an example of a charger device, in accordance with one or more examples described in this disclosure.

FIG. 8 is a block diagram illustrating an example of a charger device, in accordance with one or more examples described in this disclosure. As illustrated, charger device 42 includes processing circuitry 80, memory 82, power circuitry 84, telemetry circuitry 86, and AC/DC converter 88.

In some examples, memory 82 may store user-specific configuration data. Memory 82 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 80 can take the form one or more microprocessors, DSPs, ASICs, FPGAs, programmable logic circuitry, or the like, and the functions attributed to processing circuitry 80 herein may be embodied as hardware, firmware, software, or any combination thereof.

Telemetry circuitry 86 may include any suitable hardware, firmware, software or any combination thereof for enabling communication between charger device 42 and another device, such as one or more servers 28 of cloud 26, in-use device 40A, replacement device 40B, and patient device 24. Telemetry circuitry 86 may send and/or receive communication with the aid of an antenna, which may be internal and/or external to charger device 42. Telemetry circuitry 86 may be configured to communicate via wired or wireless communication techniques. Examples of local wireless communication techniques that may be employed to facilitate communication between charger device 42 and another computing device include RF communication according to IEEE 802.11, Bluetooth, or BLE specification sets, infrared communication, e.g., according to an IrDA standard, near field communication (NFC), or other standard or proprietary telemetry protocols. Telemetry circuitry 86 may also provide connectivity with a carrier network for access to cloud 26. In this manner, other devices may be capable of communicating with charger device 42.

AC/DC converter 88 may be configured to receive AC voltage and current through a wall socket in the home of patient 12 and convert the AC voltage and current to DC voltage and current. AC/DC converter 88 may thus provide power to the components of charger device 42.

Power circuitry 84 may be configured to provide power to medical device 51. For example, power circuitry 84 may include an inductive coil that outputs power to medical device 51 for charging its battery. In some examples, power circuitry 84 and telemetry circuitry 86 may use the same coil for wireless communication and power delivery. In some examples, power circuitry 84 and telemetry circuitry 86 may share the same cable to deliver power and communicate.

Figure 9:
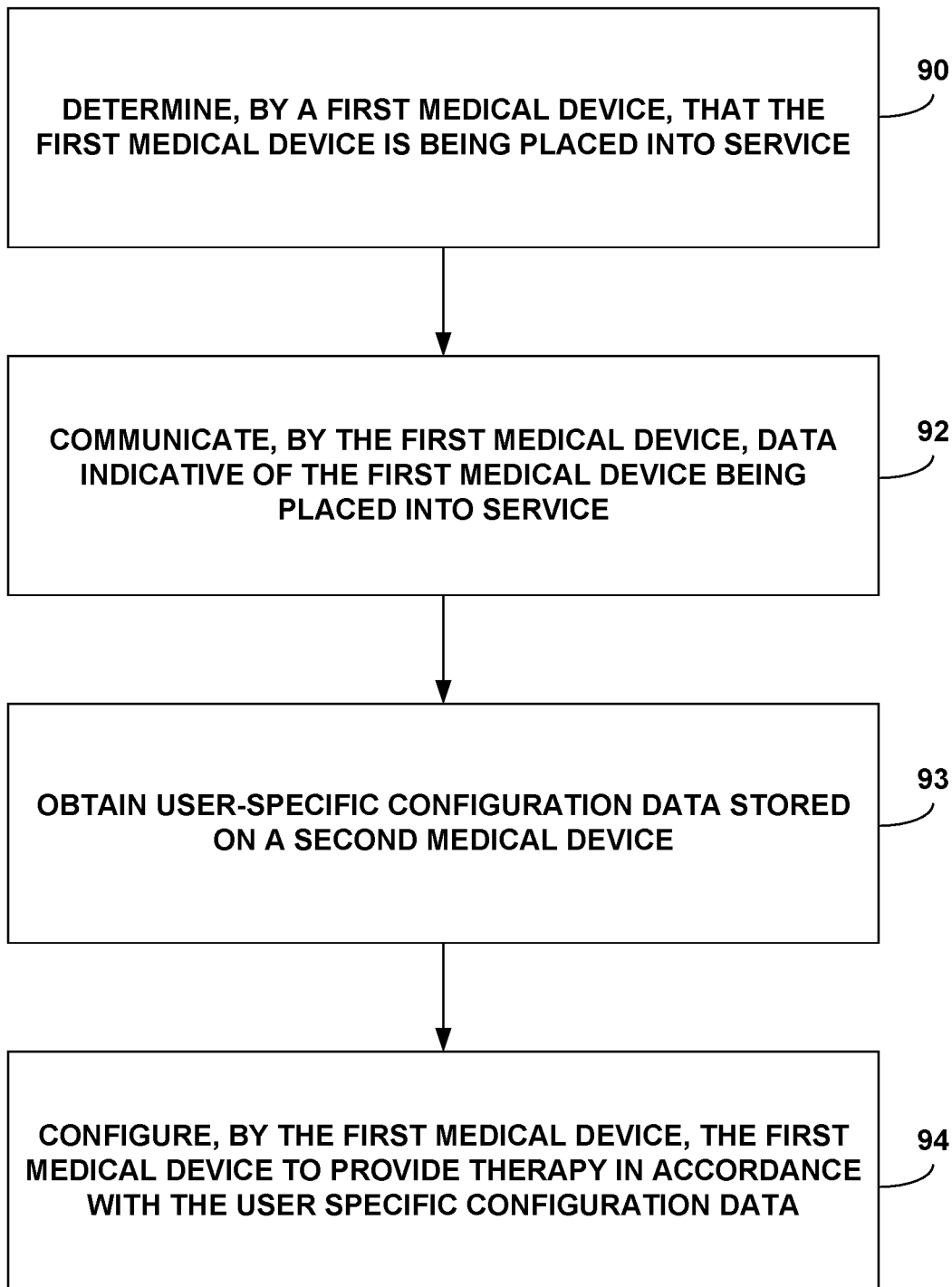
FIG. 9 is a flowchart illustrating an example process for automatic configuration based on placement into service, in accordance with one or more examples described in this disclosure.

FIG. 9 is a flowchart illustrating an example process for automatic configuration based on placement into service, in accordance with one or more examples described in this disclosure. As illustrated in FIG. 9, a first medical device (e.g., replacement device 40B) may determine that it is being placed into service to provide medical therapy to a patient (90). The first medical device may be a replacement device for a second medical device (e.g., in-use device 40A) that was previously placed into service to provide medical therapy to a patient in accordance with user-specific configuration data stored on the second medical device.

In some examples, the first medical device and the second medical device may share a number of similarities. For example, they may serve the same purpose (e.g., physiological characteristic monitoring and/or therapeutic substance delivery), have the same model number (e.g., 670G), etc. In some examples, the first and second medical devices may each be an insulin delivery device (e.g., insulin pump 14 or 30) or may each be a portion of an insulin delivery device (e.g., durable portion 32 of insulin pump 30). In some other examples, the first and second medical device may each be a glucose level monitor (e.g., monitoring device 20).

There are various ways in which the first medical device may determine that it is being placed into service. For example, the first medical device may make this determination based on one or more of the following: determining that a first portion of the first medical device (e.g., durable portion 32) is removably attached to a second portion of the first medical device (e.g., consumable portion 34), determining activation of a cannula insertion mechanism associated with the first medical device, processing a signal from a skin contact sensor associated with the first medical device, determining actuation of a mechanical switch between the first medical device and the patient, and determining that an integrated glucose sensor associated with the first medical device is in contact with interstitial fluid.

The user-specific configuration data may include parameters, settings, and/or other forms of data that vary from user to user. Examples of the user-specific configuration data include one or more of the following: information indicative of insulin-on-board, a safe basal rate, one or more insulin delivery rate limits, one or more glucose sensor calibration factors, an insulin sensitivity factor, and a history of insulin delivery.

Upon determining that it is being placed into service, the first medical device may communicate data indicative of the first medical device being placed into service (92). For example, the data may include a request for the user-specific configuration data.

In some examples, the first medical device may communicate the data to the second medical device. In some other examples, the first medical device may communicate the data to one or more intermediate devices (e.g., patient device 24, charger device 42, and/or one or more servers 28).

After communicating the data indicative of the first medical device being placed into service, the first medical device may obtain the user-specific configuration data stored on the second medical device (93). In some examples, the first medical device may obtain the user-specific configuration data directly from the second medical device. For example, the first medical device may request user-specific configuration data from the second medical device, which responds with its user-specific configuration data. In some other examples, the first medical device may obtain the user-specific configuration data through an intermediate device that obtains it from the second medical device. For example, after the first medical device communicates that its cannula insertion mechanism has been activated, patient device 24 may obtain the user-specific configuration data from the second medical device and communicate the configuration data to the first medical device.

At any time prior to obtaining the user-specific configuration data, the first medical device may establish a communication link through which the first medical device obtains the user-specific configuration data. For example, when the first medical device is being placed into service, the patient may provide user input to establish a network connection between the first medical device and the second medical device or an intermediate device.

The first medical device may configure itself to provide therapy in accordance with the user-specific configuration data (94). Thus, obtaining the user-specific configuration data may initiate a process for automatically configuring the first medical device.

Figure 10:
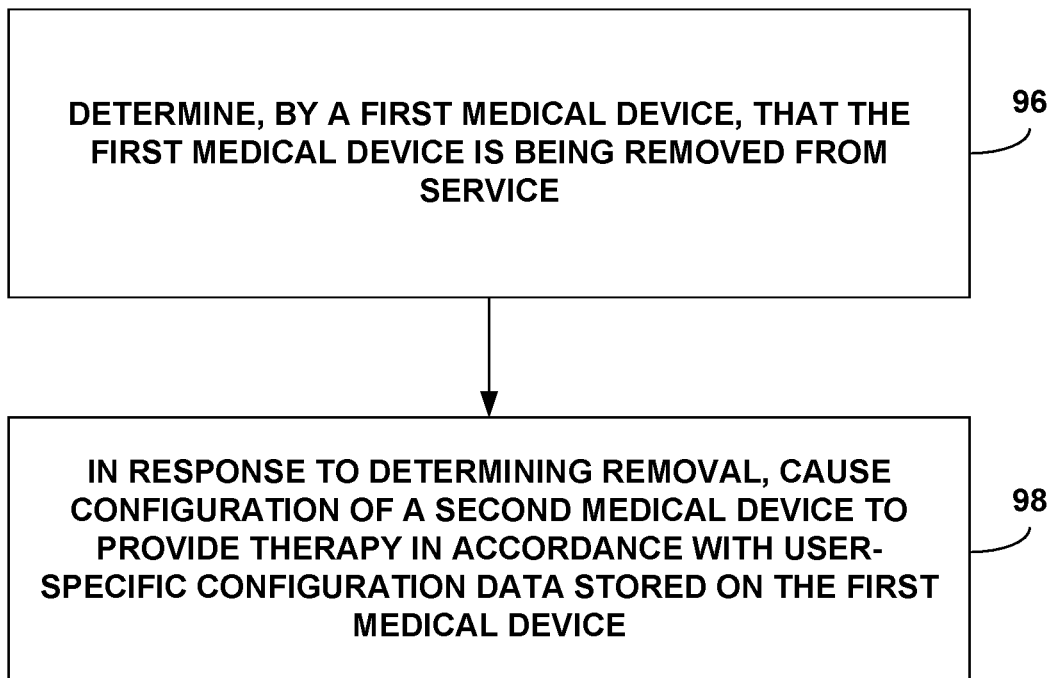
FIG. 10 is a flowchart illustrating an example process for automatic configuration based on removal from service, in accordance with one or more examples described in this disclosure.

FIG. 10 is a flowchart illustrating an example process for automatic configuration based on removal from service, in accordance with one or more examples described in this disclosure. As illustrated in FIG. 10, a first medical device (e.g., in-use device 40A) may determine that it is being removed from service (96). The first medical device may have been previously placed into service to provide therapy to a patient in accordance with user-specific configuration data stored on the first medical device. In some examples, the first medical device is to be replaced with a second medical device (e.g., replacement device 40B) that is a replacement device for the first medical device.

In some examples, the first medical device and the second medical device may share a number of similarities. For example, they may serve the same purpose (e.g., physiological characteristic monitoring and/or therapeutic substance delivery), have the same model number (e.g., 670G), etc. In some examples, the first and second medical devices may each be an insulin delivery device (e.g., insulin pump 14 or 30) or may each be a portion of an insulin delivery device (e.g., durable portion 32 of insulin pump 30). In some other examples, the first and second medical device may each be a glucose level monitor (e.g., monitoring device 20).

There are various ways in which the first medical device may determine that it is being removed from service. For example, the first medical device may make this determination based on one or more of the following: that a first portion of the first medical device (e.g., durable portion 32) is separated from a second portion of the first medical device (e.g., consumable portion 34), determining removal of a cannula associated with the first medical device, processing a signal from a skin contact sensor associated with the first medical device, detecting a reset of a mechanical switch between the first medical device and the patient, determining that an integrated glucose sensor associated with the first medical device is no longer in contact with interstitial fluid, and receiving user input.

The user-specific configuration data may include parameters, settings, and/or other forms of data that vary from user to user. Examples of the user-specific configuration data include one or more of the following: information indicative of insulin-on-board, a safe basal rate, one or more insulin delivery rate limits, one or more glucose sensor calibration factors, an insulin sensitivity factor, and a history of insulin delivery.

In response to determining that it is being removed from service, the first medical device may cause configuration of the second medical device to provide therapy to the patient in accordance with the user-specific configuration data (98). Causing configuration of the second medical device may include the first medical device communicating the user-specific configuration data toward the second medical device. Thus, the second medical device obtaining the user-specific configuration data may initiate a process for automatically configuring the second medical device.

In some examples, the first medical device may communicate the user-specific configuration data directly to the second medical device. For example, the first medical device may transmit data indicative of removal from service, the second medical device may respond with a request for the user-specific configuration data, and the first medical device may communicate the requested data to the second medical device. In some other examples, the first medical device may communicate the user-specific configuration data to one or more intermediate devices (e.g., patient device 24, charger device 42, and/or one or more servers 28) from which the second medical device obtains the user-specific configuration data. For example, the first medical device may communicate the user-specific configuration data to patient device 24, which forwards it to the second medical device.

At any time prior to communicating the user-specific configuration data, the first medical device may establish a communication link through which the first medical device communicates the user-specific configuration data. For example, when the first medical device is being removed from service, the patient may provide user input to establish a network connection between the first medical device and the second medical device.

Figure 11:
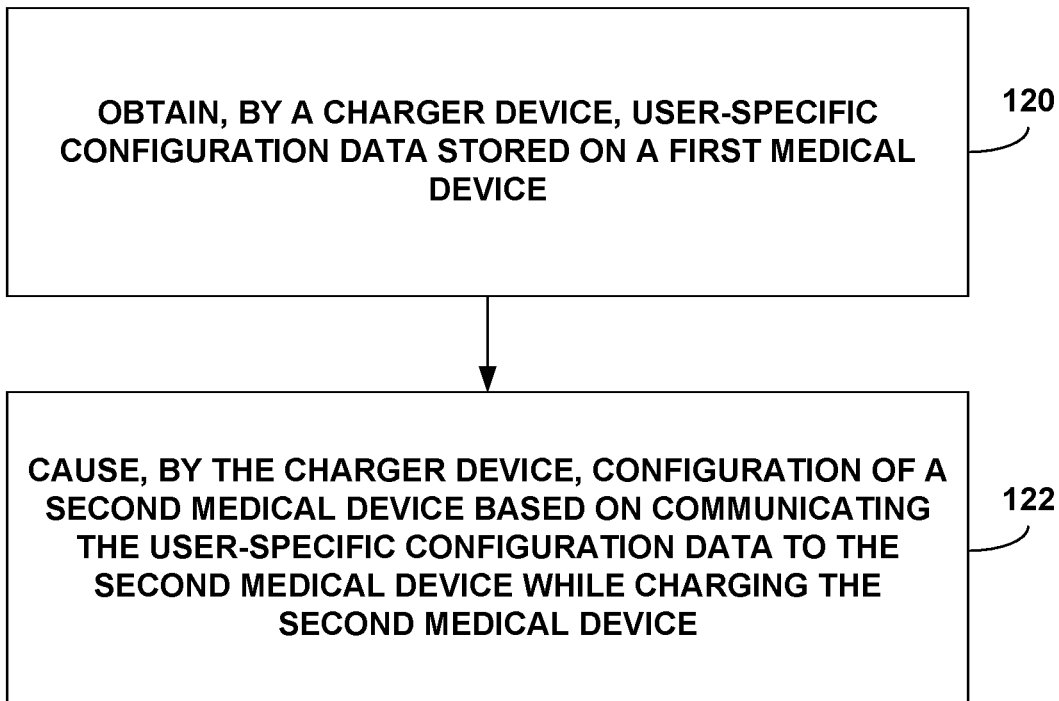
FIG. 11 is a flowchart illustrating an example process for automatic configuration involving a networked charger device, in accordance with one or more examples described in this disclosure.

FIG. 11 is a flowchart illustrating an example process for automatic configuration involving a networked charger device, in accordance with one or more examples described in this disclosure. FIG. 11 illustrates an example of transferring user-specific configuration data via charger device 42.

Charger device 42 may obtain, from one or more server computing devices, user-specific configuration data stored on a first medical device (e.g., in-use device 40A) that is configured to provide therapy to a patient in accordance with the user-specific configuration data (120). Charger device 42 may obtain the user-specific configuration data using various communication protocols (e.g., push or pull) and with or without regard for whether an update to the user-specific configuration data is available. For example, the one or more server computing devices may be configured to automatically push any updates to charger device 42. As another example, charger device 42 may periodically poll the one or more server computing devices to determine whether there is an update for charger device 42 to retrieve. As yet another example, the one or more server computing devices may continuously stream user-specific configuration data (updated or not) to charger device 42. As still another example, charger device 42 may periodically retrieve any user-specific configuration data (updated or not) stored on the one or more server computing devices.

The user-specific configuration data may include parameters, settings, and/or other forms of data that vary from user to user. Examples of the user-specific configuration data include one or more of the following: information indicative of insulin-on-board, a safe basal rate, one or more insulin delivery rate limits, one or more glucose sensor calibration factors, an insulin sensitivity factor, and a history of insulin delivery.

Charger device 42 may cause configuration of a second medical device (e.g., replacement device 40B) based on communicating the user-specific configuration data to the second medical device while the second medical device is being charged by charger device 42 (122). The second medical device may be a replacement device for the first medical device.

In some examples, the example process of FIG. 11 may comprise tasks to help ensure that the second medical device has the most up-to-date user-specific configuration data when the second medical device is being placed into service. For example, charger device 42 may determine that the second medical device is being placed into service (e.g., by detecting removal of the second medical device from charger device 42, by obtaining data indicative of the first medical device being removed from service, or by any other technique disclosed herein). After determining that the second medical device is being placed into service, charger device 42 may obtain, from the one or more server computing devices, an update to the user-specific configuration data stored on the first medical device. Charger device 42 may cause configuration of the second medical device based on communicating the update to the second medical device.

In some examples, charger device 42 may be configured to charge the second medical device based on electromagnetic induction. In some other examples, charger device 42 may be configured to charge the second medical device based on an electrical connection.

In some examples, the first medical device and the second medical device may share a number of similarities. For example, they may serve the same purpose (e.g., physiological characteristic monitoring and/or therapeutic substance delivery), have the same model number (e.g., 670G), etc. In some examples, the first and second medical devices may each be an insulin delivery device (e.g., insulin pump 14 or 30) or may each be a portion of an insulin delivery device (e.g., durable portion 32 of insulin pump 30). In some other examples, the first and second medical device may each be a glucose level monitor (e.g., monitoring device 20).

The following describes some example techniques that may be utilized separately or together in any combination.

Example 1. A method for automatically configuring a medical device with user-specific configuration data, the method comprising determining, by a first medical device, that the first medical device is being placed into service to provide medical therapy to a patient, wherein the first medical device is a replacement medical device for a second medical device that was previously placed into service to provide medical therapy to the patient in accordance with user-specific configuration data stored on the second medical device, communicating, by the first medical device, data indicative of the first medical device being placed into service, after communicating the data indicative of the first medical device being placed into service, obtaining, by the first medical device, the user-specific configuration data stored on the second medical device, and configuring, by the first medical device, the first medical device to provide therapy in accordance with the obtained user-specific configuration data.

Example 2. The method of example 1, further comprising: prior to obtaining the user-specific configuration data, establishing a communication link through which the first medical device obtains the user-specific configuration data.

Example 3. The method of any of examples 1 and 2, wherein the user-specific configuration data comprises at least one of a group including information indicative of insulin-on-board, a safe basal rate, one or more insulin delivery rate limits, one or more glucose sensor calibration factors, an insulin sensitivity factor, and a history of insulin delivery.

Example 4. The method of any of examples 1-3, wherein the first medical device comprises a first portion and a second portion, and wherein determining that the first medical device is being placed into service comprises determining that the first portion is removably attached to the second portion.

Example 5. The method of any of examples 1-4, wherein determining that the first medical device is being placed into service comprises determining activation of a cannula insertion mechanism associated with the first medical device.

Example 6. The method of any of examples 1-5, wherein determining that the first medical device is being placed into service comprises processing a signal from a skin contact sensor associated with the first medical device.

Example 7. The method of any of examples 1-6, wherein determining that the first medical device is being placed into service comprises determining actuation of a mechanical switch between the first medical device and the patient.

Example 8. The method of any of examples 1-7, wherein determining that the first medical device is being placed into service comprises determining that a glucose sensor is in contact with interstitial fluid.

Example 9. The method of any of examples 1-8, wherein obtaining the user-specific configuration data comprises obtaining the user-specific configuration data through an intermediate device that obtains the user-specific configuration data from the second medical device.

Example 10. The method of any of examples 1-9, wherein the data indicative of the first medical device being placed into service comprises a request for the user-specific configuration data.

Example 11. A system for automatically configuring a medical device with user-specific configuration data, the system comprising one or more processors, and one or more processor-readable storage media storing instructions which, when executed by the one or more processors, cause performance of determining that a first medical device is being placed into service to provide medical therapy to a patient, wherein the first medical device is a replacement medical device for a second medical device that was previously placed into service to provide medical therapy to the patient in accordance with user-specific configuration data stored on the second medical device, communicating data indicative of the first medical device being placed into service, after communicating the data indicative of the first medical device being placed into service, obtaining the user-specific configuration data stored on the second medical device, and configuring the first medical device to provide therapy in accordance with the obtained user-specific configuration data.

Example 12. The system of example 11, wherein the user-specific configuration data comprises at least one of a group including information indicative of insulin-on-board, a safe basal rate, one or more insulin delivery rate limits, one or more glucose sensor calibration factors, an insulin sensitivity factor, and a history of insulin delivery.

Example 13. The system of any of examples 11 and 12, wherein the first medical device comprises a first portion and a second portion, and wherein determining that the first medical device is being placed into service comprises determining that the first portion is removably attached to the second portion.

Example 14. The system of any of examples 11-13, wherein determining that the first medical device is being placed into service comprises determining activation of a cannula insertion mechanism associated with the first medical device.

Example 15. The system of any of examples 11-14, wherein determining that the first medical device is being placed into service comprises processing a signal from a skin contact sensor associated with the first medical device.

Example 16. The system of any of examples 11-15, wherein determining that the first medical device is being placed into service comprises determining actuation of a mechanical switch between the first medical device and the patient.

Example 17. The system of any of examples 11-16, wherein determining that the first medical device is being placed into service comprises determining that a glucose sensor is in contact with interstitial fluid.

Example 18. The system of any of examples 11-17, wherein obtaining the user-specific configuration data comprises obtaining the user-specific configuration data through an intermediate device that obtains the user-specific configuration data from the second medical device.

Example 19. The system of any of examples 11-18, wherein the data indicative of the first medical device being placed into service comprises a request for the user-specific configuration data.

Example 20. One or more non-transitory processor-readable storage media storing instructions which, when executed by one or more processors, cause performance of determining that a first medical device is being placed into service to provide medical therapy to a patient, wherein the first medical device is a replacement medical device for a second medical device that was previously placed into service to provide medical therapy to the patient in accordance with user-specific configuration data stored on the second medical device, communicating data indicative of the first medical device being placed into service, after communicating the data indicative of the first medical device being placed into service, obtaining the user-specific configuration data stored on the second medical device, and configuring the first medical device to provide therapy in accordance with the obtained user-specific configuration data.

Example 21. A method for automatically configuring a medical device with user-specific configuration data, the method comprising determining, by a first medical device, that the first medical device is being removed from service, wherein the first medical device was previously placed into service to provide therapy to a patient in accordance with user-specific configuration data stored on the first medical device, and wherein the first medical device is to be replaced with a second medical device that is a replacement medical device for the first medical device, and causing, by the first medical device in response to determining that the first medical device is being removed from service, configuration of the second medical device to provide therapy to the patient in accordance with the user-specific configuration data, wherein causing configuration of the second medical device comprises communicating the user-specific configuration data toward the second medical device.

Example 22. The method of example 21, further comprising prior to communicating the user-specific configuration data toward the second medical device, establishing a communication link through which the first medical device communicates the user-specific configuration.

Example 23. The method of any of examples 21 and 22, wherein the user-specific configuration data comprises at least one of a group including information indicative of insulin-on-board, a safe basal rate, one or more insulin delivery rate limits, one or more glucose sensor calibration factors, an insulin sensitivity factor, and a history of insulin delivery.

Example 24. The method of any of examples 21-23, wherein the first medical device comprises a first portion and a second portion, and wherein determining that the first medical device is being removed from service comprises determining that the first portion is separated from the second portion.

Example 25. The method of any of examples 21-24, wherein determining that the first medical device is being removed from service comprises determining removal of a cannula associated with the first medical device.

Example 26. The method of any of examples 21-25, wherein determining that the first medical device is being removed from service comprises processing a signal from a skin contact sensor associated with the first medical device.

Example 27. The method of any of examples 21-26, wherein determining that the first medical device is being removed from service comprises detecting a reset of a mechanical switch between the first medical device and the patient.

Example 28. The method of any of examples 21-27, wherein determining that the first medical device is being removed from service comprises determining that a glucose sensor is no longer in contact with interstitial fluid.

Example 29. The method of any of examples 21-28, wherein determining that the first medical device is being removed from service comprises receiving user input.

Example 30. The method of any of examples 21-29, wherein communicating the user-specific configuration data toward the second medical device comprises communicating the user-specific configuration data to an intermediate device.

Example 31. A system for automatically configuring a medical device with user-specific configuration data, the system comprising one or more processors, and one or more processor-readable storage media storing instructions which, when executed by the one or more processors, cause performance of determining that a first medical device is being removed from service, wherein the first medical device was previously placed into service to provide therapy to a patient in accordance with user-specific configuration data stored on the first medical device, and wherein the first medical device is to be replaced with a second medical device that is a replacement medical device for the first medical device, and in response to determining that the first medical device is being removed from service, causing configuration of the second medical device to provide therapy to the patient in accordance with the user-specific configuration data, wherein causing configuration of the second medical device comprises communicating the user-specific configuration data toward the second medical device.

Example 32. The system of example 31, wherein the user-specific configuration data comprises at least one of a group including information indicative of insulin-on-board, a safe basal rate, one or more insulin delivery rate limits, one or more glucose sensor calibration factors, an insulin sensitivity factor, and a history of insulin delivery.

Example 33. The system of any of examples 31 and 32, wherein the first medical device comprises a first portion and a second portion, and wherein determining that the first medical device is being removed from service comprises determining that the first portion is separated from the second portion.

Example 34. The system of any of examples 31-33, wherein determining that the first medical device is being removed from service comprises determining removal of a cannula associated with the first medical device.

Example 35. The system of any of examples 31-34, wherein determining that the first medical device is being removed from service comprises processing a signal from a skin contact sensor associated with the first medical device.

Example 36. The system of any of examples 31-35, wherein determining that the first medical device is being removed from service comprises detecting a reset of a mechanical switch between the first medical device and the patient.

Example 37. The system of any of examples 31-36, wherein determining that the first medical device is being removed from service comprises determining that a glucose sensor is no longer in contact with interstitial fluid.

Example 38. The system of any of examples 31-37, wherein determining that the first medical device is being removed from service comprises receiving user input.

Example 39. The system of any of examples 31-38, wherein communicating the user-specific configuration data toward the second medical device comprises communicating the user-specific configuration data to an intermediate device.

Example 40. One or more non-transitory processor-readable storage media storing instructions which, when executed by one or more processors, cause performance of determining that a first medical device is being removed from service, wherein the first medical device was previously placed into service to provide therapy to a patient in accordance with user-specific configuration data stored on the first medical device, and wherein the first medical device is to be replaced with a second medical device that is a replacement medical device for the first medical device, and in response to determining that the first medical device is being removed from service, causing configuration of the second medical device to provide therapy to the patient in accordance with the user-specific configuration data, wherein causing configuration of the second medical device comprises communicating the user-specific configuration data toward the second medical device.

Example 41. A method for automatically configuring a medical device with user-specific configuration data, the method comprising obtaining, by a charger device from one or more server computing devices, user-specific configuration data stored on a first medical device that is configured to provide therapy to a patient in accordance with the user-specific configuration data, and causing, by the charger device, configuration of a second medical device based on communicating the user-specific configuration data to the second medical device while the second medical device is being charged by the charger device, wherein the second medical device is a replacement device for the first medical device.

Example 42. The method of example 41, further comprising determining, by the charger device, that the second medical device is being placed into service, after determining that the second medical device is being placed into service, obtaining, by the charger device from the one or more server computing devices, an update to the user-specific configuration data stored on the first medical device, and causing, by the charger device, configuration of the second medical device based on communicating the update to the second medical device.

Example 43. The method of example 42, wherein determining that the second medical device is being placed into service comprises detecting removal of the second medical device from the charger device.

Example 44. The method of any of examples 42 and 43, wherein determining that the second medical device is being placed into service comprises obtaining data indicative of the first medical device being removed from service.

Example 45. The method of any of examples 41-44, wherein the charger device is configured to charge the second medical device based on electromagnetic induction.

Example 46. The method of any of examples 41-45, wherein the user-specific configuration data comprises at least one of a group including information indicative of insulin-on-board, a safe basal rate, one or more insulin delivery rate limits, one or more glucose sensor calibration factors, an insulin sensitivity factor, and a history of insulin delivery.

Example 47. The method of any of examples 41-46, wherein each of the first medical device and the second medical device includes an insulin pump.

Example 48. A system for automatically configuring a medical device with user-specific configuration data, the system comprising one or more processors, and one or more processor-readable storage media storing instructions which, when executed by the one or more processors, cause performance of obtaining, from one or more server computing devices, user-specific configuration data stored on a first medical device that is configured to provide therapy to a patient in accordance with the user-specific configuration data, and causing configuration of a second medical device based on communicating the user-specific configuration data to the second medical device while the second medical device is being charged by the charger device, wherein the second medical device is a replacement device for the first medical device.

Example 49. The system of example 48, wherein the instructions comprise instructions which, when executed by the one or more processors, cause performance of determining that the second medical device is being placed into service, after determining that the second medical device is being placed into service, obtaining, from the one or more server computing devices, an update to the user-specific configuration data stored on the first medical device, and causing configuration of the second medical device based on communicating the update to the second medical device.

Example 50. The system of example 49, wherein determining that the second medical device is being placed into service comprises detecting removal of the second medical device from the charger device.

Example 51. The system of any of examples 49 and 50, wherein determining that the second medical device is being placed into service comprises obtaining data indicative of the first medical device being removed from service.

Example 52. The system of any of examples 48-51, wherein the charger device is configured to charge the second medical device based on electromagnetic induction.

Example 53. The system of any of examples 48-52, wherein the user-specific configuration data comprises at least one of a group including information indicative of insulin-on-board, a safe basal rate, one or more insulin delivery rate limits, one or more glucose sensor calibration factors, an insulin sensitivity factor, and a history of insulin delivery.

Example 54. The system of any of examples 48-53, wherein each of the first medical device and the second medical device includes an insulin pump.

Example 55. One or more non-transitory processor-readable storage media storing instructions which, when executed by one or more processors, cause performance of obtaining, from one or more server computing devices, user-specific configuration data stored on a first medical device that is configured to provide therapy to a patient in accordance with the user-specific configuration data, and causing configuration of a second medical device based on communicating the user-specific configuration data to the second medical device while the second medical device is being charged by the charger device, wherein the second medical device is a replacement device for the first medical device.

Example 56. The one or more non-transitory processor-readable storage media of example 55, wherein the instructions comprise instructions which, when executed by the one or more processors, cause performance of determining that the second medical device is being placed into service, after determining that the second medical device is being placed into service, obtaining, from the one or more server computing devices, an update to the user-specific configuration data stored on the first medical device, and causing configuration of the second medical device based on communicating the update to the second medical device.

Example 57. The one or more non-transitory processor-readable storage media of example 56, wherein determining that the second medical device is being placed into service comprises detecting removal of the second medical device from the charger device.

Example 58. The one or more non-transitory processor-readable storage media of any of examples 56 and 57, wherein determining that the second medical device is being placed into service comprises obtaining data indicative of the first medical device being removed from service.

Example 59. The one or more non-transitory processor-readable storage media of any of examples 55-58, wherein the charger device is configured to charge the second medical device based on electromagnetic induction.

Example 60. The one or more non-transitory processor-readable storage media of any of examples 55-59, wherein the user-specific configuration data comprises at least one of a group including information indicative of insulin-on-board, a safe basal rate, one or more insulin delivery rate limits, one or more glucose sensor calibration factors, an insulin sensitivity factor, and a history of insulin delivery.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors 28 of cloud 26, one or more processors of patient device 24, one or more processors of insulin pump 14, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. A method for automatically configuring a medical device with user-specific configuration data, the method comprising:

determining, by a first medical device, that the first medical device is being placed into service to provide medical therapy to a patient, wherein the first medical device is a replacement medical device for a second medical device that was previously placed into service to provide medical therapy to the patient in accordance with user-specific configuration data stored on the second medical device, wherein determining that the first medical device is being placed into service comprises at least one of a group including:

responsive to receiving user input, establishing a communication link through which the first medical device obtains the user-specific configuration data;
determining that a first portion of the first medical device is removably attached to a second portion of the first medical device;
determining activation of a cannula insertion mechanism associated with the first medical device;
processing a signal from a skin contact sensor associated with the first medical device;
determining actuation of a mechanical switch between the first medical device and the patient; and
determining that a glucose sensor is in contact with interstitial fluid;

communicating, by the first medical device, data indicative of the first medical device being placed into service;

after communicating the data indicative of the first medical device being placed into service, obtaining, by the first medical device, the user-specific configuration data stored on the second medical device; and configuring, by the first medical device, the first medical device to provide therapy in accordance with the obtained user-specific configuration data.

2. The method of claim 1, further comprising:
prior to obtaining the user-specific configuration data, establishing a communication link through which the first medical device obtains the user-specific configuration data.

3. The method of claim 1, wherein the user-specific configuration data comprises at least one of a group including information indicative of insulin-on-board, a safe basal rate, one or more insulin delivery rate limits, one or more glucose sensor calibration factors, an insulin sensitivity factor, and a history of insulin delivery.

4. The method of claim 1, wherein the first medical device comprises the first portion and the second portion, and wherein determining that the first medical device is being placed into service comprises determining that the first portion is removably attached to the second portion.

5. The method of claim 1, wherein determining that the first medical device is being placed into service comprises determining activation of the cannula insertion mechanism associated with the first medical device.

6. The method of claim 1, wherein determining that the first medical device is being placed into service comprises processing a signal from the skin contact sensor associated with the first medical device.

7. The method of claim 1, wherein determining that the first medical device is being placed into service comprises determining actuation of the mechanical switch between the first medical device and the patient.

8. The method of claim 1, wherein determining that the first medical device is being placed into service comprises determining that the glucose sensor is in contact with interstitial fluid.

9. The method of claim 1, wherein obtaining the user-specific configuration data comprises obtaining the user-specific configuration data through an intermediate device that obtains the user-specific configuration data from the second medical device.

10. The method of claim 1, wherein the data indicative of the first medical device being placed into service comprises a request for the user-specific configuration data.

11. A system for automatically configuring a medical device with user-specific configuration data, the system comprising:
one or more processors; and
one or more processor-readable storage media storing instructions which, when executed by the one or more processors, cause performance of:
determining that a first medical device is being placed into service to provide medical therapy to a patient, wherein the first medical device is a replacement medical device for a second medical device that was previously placed into service to provide medical therapy to the patient in accordance with user-specific configuration data stored on the second medical device, wherein determining that the first medical device is being placed into service comprises at least one of a group including:
responsive to receiving user input, establishing a communication link through which the first medical device obtains the user-specific configuration data;
determining that a first portion of the first medical device is removably attached to a second portion of the first medical device;
determining activation of a cannula insertion mechanism associated with the first medical device;
processing a signal from a skin contact sensor associated with the first medical device;
determining actuation of a mechanical switch between the first medical device and the patient; and
determining that a glucose sensor is in contact with interstitial fluid;
communicating data indicative of the first medical device being placed into service;
after communicating the data indicative of the first medical device being placed into service, obtaining the user-specific configuration data stored on the second medical device; and
configuring the first medical device to provide therapy in accordance with the obtained user-specific configuration data.

12. The system of claim 11, wherein the user-specific configuration data comprises at least one of a group including information indicative of insulin-on-board, a safe basal rate, one or more insulin delivery rate limits, one or more glucose sensor calibration factors, an insulin sensitivity factor, and a history of insulin delivery.

13. The system of claim 11, wherein the first medical device comprises the first portion and the second portion, and wherein determining that the first medical device is being placed into service comprises determining that the first portion is removably attached to the second portion.

14. The system of claim 11, wherein determining that the first medical device is being placed into service comprises determining activation of the cannula insertion mechanism associated with the first medical device.

15. The system of claim 11, wherein determining that the first medical device is being placed into service comprises processing a signal from the skin contact sensor associated with the first medical device.

16. The system of claim 11, wherein determining that the first medical device is being placed into service comprises determining actuation of the mechanical switch between the first medical device and the patient.

17. The system of claim 11, wherein determining that the first medical device is being placed into service comprises determining that the glucose sensor is in contact with interstitial fluid.

18. The system of claim 11, wherein obtaining the user-specific configuration data comprises obtaining the user-specific configuration data through an intermediate device that obtains the user-specific configuration data from the second medical device.

19. The system of claim 11, wherein the data indicative of the first medical device being placed into service comprises a request for the user-specific configuration data.

20. One or more non-transitory processor-readable storage media storing instructions which, when executed by one or more processors, cause performance of:
determining that a first medical device is being placed into service to provide medical therapy to a patient, wherein the first medical device is a replacement medical device for a second medical device that was previously placed into service to provide medical therapy to the patient in accordance with user-specific configuration data stored on the second medical device, wherein determining that the first medical device is being placed into service comprises at least one of a group including:
responsive to receiving user input, establishing a communication link through which the first medical device obtains the user-specific configuration data;
determining that a first portion of the first medical device is removably attached to a second portion of the first medical device;
determining activation of a cannula insertion mechanism associated with the first medical device;
processing a signal from a skin contact sensor associated with the first medical device;
determining actuation of a mechanical switch between the first medical device and the patient; and
determining that a glucose sensor is in contact with interstitial fluid;
communicating data indicative of the first medical device being placed into service;
after communicating the data indicative of the first medical device being placed into service, obtaining the user-specific configuration data stored on the second medical device; and
configuring the first medical device to provide therapy in accordance with the obtained user-specific configuration data.

* * * * *